(12) United States Patent
Seitz et al.

(10) Patent No.: US 6,225,334 B1
(45) Date of Patent: May 1, 2001

(54) GLYOXYLIC ACID DERIVATIVES

(75) Inventors: Thomas Seitz, Langenfeld; Klaus Stenzel, Düsseldorf; Ulrike Wachendorff-Neumann, Neuwied, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/214,749

(22) PCT Filed: Jul. 9, 1997

(86) PCT No.: PCT/EP97/03644

§ 371 Date: Jan. 11, 1999

§ 102(e) Date: Jan. 11, 1999

(87) PCT Pub. No.: WO98/03474

PCT Pub. Date: Jan. 29, 1998

(30) Foreign Application Priority Data

| Jul. 22, 1996 | (DE) | 196 29 466 |
| Jul. 22, 1996 | (DE) | 196 29 463 |
| Jul. 22, 1996 | (DE) | 196 29 464 |
| Jul. 22, 1996 | (DE) | 196 29 465 |

(51) Int. Cl.$^7$ .................. A61K 31/405; C07C 69/612; C07D 209/14

(52) U.S. Cl. .................. 514/415; 549/74; 549/491; 560/129; 560/251; 560/252; 560/256; 548/491; D22/122

(58) Field of Search .................. 560/129, 251, 560/252, 256; 548/491

(56) References Cited

U.S. PATENT DOCUMENTS 5,709,867 * 1/1998 Bernardon .

FOREIGN PATENT DOCUMENTS

| 0 658 549 | 6/1995 | (EP) . |
| 51-91284 * | 8/1976 | (JP) . |
| 94 26700 | 11/1994 | (WO) . |
| 96 23763 | 8/1996 | (WO) . |

* cited by examiner

Primary Examiner—Joseph K. McKane
(74) Attorney, Agent, or Firm—Norris McLaughlin & Marcus

(57) ABSTRACT

The invention concerns novel glyoxylic acid derivatives, a process for their preparation and their use as pesticides.

15 Claims, No Drawings

GLYOXYLIC ACID DERIVATIVES

This application is a 371 of PCT/EP97/03644 filed Jul. 9, 1997.

The invention relates to novel glyoxylic acid derivatives, to a process for their preparation and to their use as pesticides.

This invention provides novel compounds of the general formula (I)

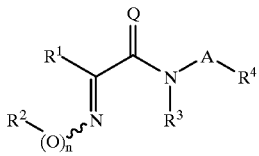

in which
A represents a single bond or optionally substituted alkylene,
Q represents oxygen or sulphur,
n represents a number 0 or 1,
$R^1$ represents cycloalkyl, cycloalkenyl, aryl or heterocyclyl, each of which is optionally substituted,
$R^2$, in the case that n represents the number 1, represents one of the groupings below:

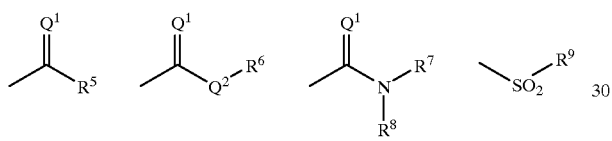

or, in the case that n represents the number 0,
$R^2$ represents hydroxyl, amino, or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted,
or, in the case that n represents the number 0 and
$R^1$ represents optionally substituted benzoheterocyclyl which is attached on the benzene ring and has one, two or three heteroatoms (but at most one heteroatom representing oxygen), or
$R^1$ represents a tricycle

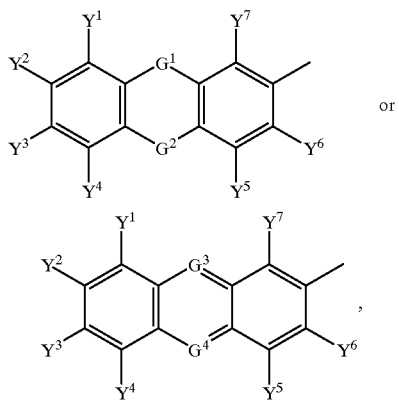

in which
$G^1$ and $G^2$ independently of one another represent a single bond, alkanediyl, alkenediyl, oxygen, sulphur, —NH—, -N(alkyl)- or carbonyl,
$G^3$ and $G^4$ independently of one another each represent nitrogen or a grouping

and
$Y^1$, $Y^2$, $Y^3$, $Y^4$, $Y^5$, $Y^6$, $Y^7$ and $Y^8$ independently of one another each represent hydrogen, halogen, cyano, nitro, or represent alkyl, alkoxy, alkylamino, dialkylamino, alkylthio, alkylsulphinyl, alkylsulphonyl or cycloalkyl, each of which is optionally substituted, or
$R^2$ then represents hydroxyl, amino or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted, or represents one of the groupings below:

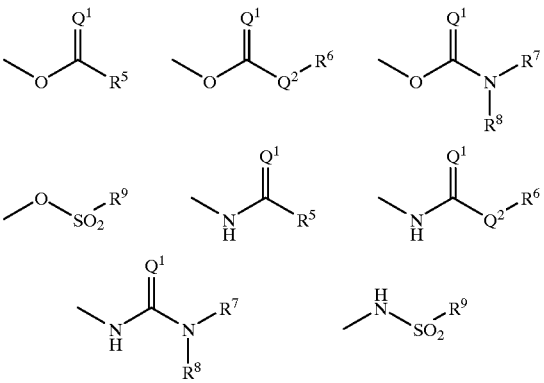

$Q^1$ and $Q^2$ independently of one another each represent oxygen or sulphur,
$R^5$ represents hydrogen or represents optionally substituted alkyl or aryl,
$R^6$ represents optionally substituted alkyl or aryl,
$R^7$ represents hydrogen or optionally substituted alkyl or aryl,
$R^8$ represents optionally substituted alkyl or aryl, or
$R^7$ and $R^8$ together with the linking nitrogen atom represent an optionally alkyl-substituted heterocyclic ring,
$R^9$ represents optionally substituted alkyl, dialkylamino, saturated heterocyclyl which is attached via nitrogen or aryl,
$R^3$ represents hydrogen or represents alkyl, alkenyl, alkinyl or cycloalkyl, each of which is optionally substituted,
$R^4$ represents cycloalkyl, cycloalkenyl, aryl or heterocyclyl, each of which is optionally substituted.

In the definitions, the saturated or unsaturated hydrocarbon chains, such as alkyl, alkanediyl, alkenyl or alkinyl, are in each case straight-chain or branched, including a in combination with heteroatoms, such as an alkoxy, alkylthio or alkylamino.

Halogen generally represents fluorine, chlorine, bromine or iodine, preferably fluorine, chlorine or bromine, in particular fluorine or chlorine.

Aryl represents aromatic mono- or polycyclic hydrocarbon rings, such as, for example, phenyl, naphthyl, anthranyl, phenanthryl, preferably phenyl or naphthyl, in particular phenyl.

Heterocyclyl represents saturated or unsaturated, and also aromatic, annular compounds in which at least one ring member is a heteroatom, i.e. an atom different from carbon. If the ring contains a plurality of heteroatoms, these may be identical or different. Preferred heteroatoms are oxygen, nitrogen or sulphur.

If appropriate, annular compounds form, together with other carbocyclic or heterocyclic fused-on or bridged rings, a polycyclic ring system. Preference is given to mono- or bicyclic ring systems, in particular to mono- or bicyclic aromatic ring systems.

Cycloalkyl represents saturated carbocyclic annular compounds which may, if appropriate, form a polycyclic ring system together with other carbocyclic fused-on or bridged rings.

Cycloalkenyl represents carbocyclic annular compounds which contain at least one double bond and which may, if appropriated, form a polycyclic ring system together with other carbocyclic fused-on or bridged rings.

Preference is given to compounds of the general formula (I-I)

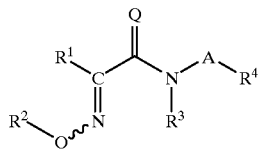

in which
A represents a single bond or optionally substituted alkylene,
Q represents oxygen or sulphur,
$R^1$ represents cycloalkyl, cycloalkenyl, aryl or heterocyclyl, each of which is optionally substituted,
$R^2$ represents one of the groupings below:

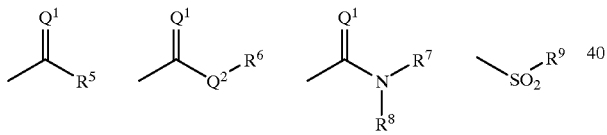

in which
$Q^1$ and $Q^2$ independently of one another each represent oxygen or sulphur,
$R^5$ represents hydrogen or optionally substituted alkyl or aryl,
$R^6$ represents optionally substituted alkyl or aryl,
$R^7$ represents hydrogen or optionally substituted alkyl or aryl,
$R^8$ represents optionally substituted alkyl or aryl, or
$R^7$ and $R^8$ together with the linking nitrogen atom represent an optionally alkyl-substituted heterocyclic ring,
$R^9$ represents optionally substituted alkyl, dialkylamino, saturated heterocyclyl which is attached via nitrogen or aryl,
$R^3$ represents hydrogen or represents alkyl, alkenyl, alkinyl or cycloalkyl, each of which is optionally substituted,
$R^4$ represents cycloalkyl, cycloalkenyl, aryl or heterocyclyl, each of which is optionally substituted.

The invention preferably provides compounds of the formula (I-I) in which
A represents a single bond or represents alkylene having 1 to 6 carbon atoms which is optionally mono- or polysubstituted by identical or different substituents, the possible substituents preferably being selected from the list below:
halogen, cyano, nitro, amino, hydroxyl, formyl, carboxyl, carbamoyl, thiocarbamoyl;
alkoxy, alkylthio, alkylsulphinyl or alkylsulphonyl having in each case 1 to 6 carbon atoms and being in each case straight-chain or branched;
alkenyl or alkenyloxy having in each case 2 to 6 carbon atoms and being in each case straight-chain or branched,
halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
cycloalkyl having 3 to 6 carbon atoms;
and also aryl or heterocyclyl, each of which is optionally mono- or polysubstituted by identical or different substituents selected from the group consisting of
halogen, cyano and straight-chain or branched alkyl having i to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms
and straight-chain or branched halogenoalkyl having 1 to 4 carbon atoms and 1 to 9 identical or different halogen atoms,
Q represents oxygen or sulphur,
$R^1$ represents aryl, cycloalkyl or cycloalkenyl having 3 to 7 carbon atoms, or heterocyclyl having 3 to 12 ring members, each of which is optionally mono- or polysubstituted by identical or different substituents, the possible substituents preferably being selected from the list below:
halogen, cyano, nitro, amino, hydroxyl, formyl, carboxyl, carbamoyl, thiocarbamoyl;
alkyl, alkoxy, alkylthio, alkylsulphinyl or alkylsulphonyl having in each case 1 to 8 carbon atoms and being in each case straight-chain or branched;
alkenyl or alkenyloxy having in each case 2 to 6 carbon atoms and being in each case straight-chain or branched;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 8 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

$R^2$ represents one of the groupings below:

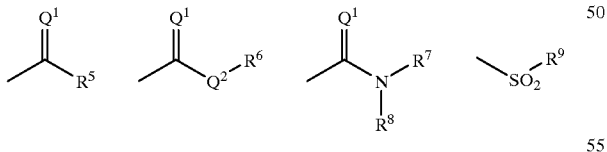

in which $Q^1$ and $Q^2$ independently of one another each represent oxygen or sulphur, $R^5$ represents hydrogen or alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^6$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^7$ represents hydrogen, alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^8$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, or $R^7$ and $R^8$ together with the linking nitrogen atom represent an optionally methyl-substituted heterocyclic ring, $R^9$ represents alkyl having 1 to 6 carbon atoms, diallylamino having in each case 1 to 4 carbon atoms in the individual alkyl moieties, heterocyclyl having 3 to 7 ring members which is attached via nitrogen or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

Cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

The invention relates in particular to compounds of the formula (I-I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents selected from the group consisting of fluorine, chlorine, cyano and methoxy, Q represents oxygen or sulphur, $R^1$ represents cyclopropyl, cyclobutyl, cyclopentyl or cyclohexyl, phenyl, naphthyl, furyl benzofuranyl, pyrrolyl, indolyl thienyl, benzothienyl, oxazolyl, isoxazolyl thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

trimethylene (propane-1,3-diyl), tetramethylene (butane-1,4diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl;

cyclopropyl, cyclobutyl, cyclopentyl or cyclohexyl;

benzyl, phenoxy, benzyloxy, or phenyl which is optionally substituted by the abovementioned substituents, $R^2$ represents one of the groupings below:

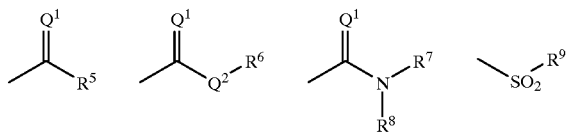

in which $Q^1$ and $Q^2$ independently of one another each represent oxygen or sulphur, $R^5$ represents hydrogen, methyl, ethyl, n- or i-propyl, n-, i-, s- or t-butyl or represents phenyl, benzyl, -phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (I-I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents selected from the group consisting of fluorine, chlorine, cyano, methoxy, Q represents oxygen or sulphur, $R^1$ represents cyclobutyl, cyclopentyl or cyclohexyl, each of which is optionally mono- to hexasubstituted, preferred substituents being those mentioned below;

represents phenyl, naphthyl, furyl, benzofuranyl, thienyl, benzothienyl, pyridyl, quinolyl, tetrahydrofuryl or perhydropyranyl, each of which is optionally mono- to trisubstituted, the possible substituents preferably being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl; cyclopropyl, cyclopentyl, cyclohexyl;

phenyl, phenoxy, benzyloxy, optionally substituted by the abovementioned substituents;

$R^2$ represents one of the groupings below:

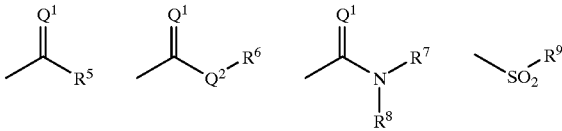

in which $Q^1$ and $Q^2$ independently of one another each represent oxygen or sulphur, $R^5$ represents hydrogen, methyl, ethyl n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl, $R^4$ represents cyclopropyl, cyclobutyl, cyclopentyl or cyclohexyl, each of which is optionally mono- to hexasubstituted, preferred substituents being those mentioned below;

represents phenyl, naphthyl, furyl, benzofuranyl, pyrrolyl, indolyl, thienyl, benzothienyl oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl hydroximinoethyl, methoximinomethyl, ethoximinomethyl, methoximinoethyl or ethoximinoethyl, represents trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

A very particularly preferred group of compounds according to the invention are those compounds of the formula (I-I) in which A represents a single bond or represents methylene, 1,1-ethylene, 1,2-ethylene, 1,1-propylene, 1,2-propylene, 1,3-propylene or 2,2-propylene, Q represents oxygen, $R^1$ represents thienyl, furanyl or phenyl which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio or represents phenyl which is substituted by 3,4-methylene- and ethylenedioxo, propane-1,3diyl and butane-1,4-diyl, each of which is optionally substituted by fluorine, or represents naphthyl, benzofuranyl or benzothienyl, $R^2$ represents one of the groupings below:

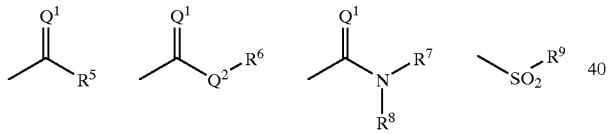

in which $Q^1$ and $Q^2$ each represent oxygen, $R^5$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl methoxy or ethoxy, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, p- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

Of very particular interest are compounds of the formula (I-I) in which the radical $R^1$ represents phenyl which is unsubstituted or substituted in position 3 and/or 4, or represents thienyl or furanyl which is unsubstituted or substituted in position 4 and/or 5, selected substituents being those mentioned above and in particular chlorine, bromine, fluorine, nitro, methylsulphonyl, phenyl, phenoxy, benzyloxy, cyclopropyl, cyclohexyl, methyl, ethyl, n-, i-propyl, n-, i-, s-, t-butyl, n-pentyl, n-hexyl, n heptyl, methoxy, ethoxy, methylthio, trifluoromethyl and trifluoromethoxy or phenyl which is substituted by 3,4-methylene- and ethylenedioxo, propane-1,3-diyl and butane-1,4-diyl, each of which is optionally substituted by fluorine, or benzofuranyl, benzothienyl or naphthyl which is substituted in position 2.

Particular preference is also given to compounds of the formula (I-I) in which $R^3$ represents hydrogen.

Particular preference is also given to compounds of the formula (I-I) in which $R^4$ represents phenyl which is substituted by methoxy in position 3 and 4.

In a group of compounds which is likewise particularly preferred, A represents —CH$_2$—CH$_2$—.

The radical definitions which, in the respective combinations or preferred combinations of radicals, are specifically mentioned for these radicals, are, independently of the combination given in each case, also replaced at will by radical definitions from other preferred ranges.

The radical definitions given above as general or as being preferred apply both to the end products of the formula (I) and also, correspondingly, to the starting materials and intermediates required in each case for the preparation.

Preferred individual compounds are shown in the tables below:

TABLE I-1

(I-Ia)

| Compound No. | $R^{10}$ | $R^{11}$ |
|---|---|---|
| I-Ia-1 | H | H |
| I-Ia-2 | H | chloro |
| I-Ia-3 | H | fluoro |
| I-Ia-4 | H | bromo |
| I-Ia-5 | H | methyl |
| I-Ia-6 | H | ethyl |
| I-Ia-7 | H | iso-propyl |
| I-Ia-8 | H | n-propyl |
| I-Ia-9 | H | n-butyl |
| I-Ia-10 | H | iso-butyl |
| I-Ia-11 | H | tert-butyl |
| I-Ia-12 | H | sec-butyl |
| I-Ia-13 | H | methoxy |
| I-Ia-14 | H | ethoxy |
| I-Ia-15 | H | methylthio |
| I-Ia-16 | H | trifluoromethyl |
| I-Ia-17 | chloro | H |
| I-Ia-18 | fluoro | H |
| I-Ia-19 | bromo | H |
| I-Ia-20 | methyl | H |
| I-Ia-21 | ethyl | H |
| I-Ia-22 | iso-propyl | H |
| I-Ia-23 | n-propyl | H |
| I-Ia-24 | n-butyl | H |
| I-Ia-25 | iso-butyl | H |
| I-Ia-26 | tert-butyl | H |
| I-Ia-27 | sec-butyl | H |
| I-Ia-28 | methoxy | H |
| I-Ia-29 | ethoxy | H |
| I-Ia-30 | methylthio | H |
| I-Ia-31 | trifluoromethyl | H |
| I-Ia-32 | chloro | chloro |
| I-Ia-33 | fluoro | fluoro |
| I-Ia-34 | bromo | bromo |
| I-Ia-35 | methyl | methyl |
| I-Ia-36 | ethyl | ethyl |
| I-Ia-37 | —OCH$_2$O— | |
| I-Ia-38 | —OCH$_2$CH$_2$O— | |
| I-Ia-39 | —OCF$_2$O— | |
| I-Ia-40 | —OCF$_2$CF$_2$O— | |
| I-Ia-41 | —(CH$_2$)$_3$— | |
| I-Ia-42 | —(CH$_2$)$_4$— | |
| I-Ia-43 | methoxy | methoxy |
| I-Ia-44 | ethoxy | ethoxy |
| I-Ia-45 | methylthio | methylthio |
| I-Ia-46 | trifluoromethyl | trifluoromethyl |
| I-Ia-47 | chloro | methyl |
| I-Ia-48 | methyl | chloro |
| I-Ia-49 | chloro | methoxy |
| I-Ia-50 | methoxy | chloro |
| I-Ia-51 | chloro | ethyl |
| I-Ia-52 | ethyl | chloro |

TABLE I-1-continued (I-Ia)

| Compound No. | $R^{10}$ | $R^{11}$ |
|---|---|---|
| I-Ia-53 | methoxy | ethoxy |
| I-Ia-54 | ethoxy | methoxy |
| I-Ia-55 | methyl | methoxy |
| I-Ia-56 | methoxy | methyl |
| I-Ia-57 | methyl | ethyl |
| I-Ia-58 | ethyl | methyl |
| I-Ia-59 | methoxy | ethyl |
| I-Ia-60 | ethyl | methoxy |
| I-Ia-61 | H | nitro |
| I-Ia-62 | H | methylsulphonyl |
| I-Ia-63 | H | phenoxy |
| I-Ia-64 | H | phenyl |
| I-Ia-65 | H | benzyloxy |
| I-Ia-66 | H | pentyl |
| I-Ia-67 | H | hexyl |
| I-Ia-68 | H | heptyl |
| I-Ia-69 | H | cyclopropyl |
| I-Ia-70 | H | cyclohexyl |

TABLE I-2

(I-Ib)

| Compound No. | $R^{12}$ | $R^{13}$ |
|---|---|---|
| I-Ib-1 | H | H |
| I-Ib-2 | H | chloro |
| I-Ib-3 | H | fluoro |
| I-Ib-4 | H | bromo |
| I-Ib-5 | H | methyl |
| I-Ib-6 | H | ethyl |
| I-Ib-7 | H | iso-propyl |
| I-Ib-8 | H | n-propyl |
| I-Ib-9 | H | n-butyl |
| I-Ib-10 | H | iso-butyl |
| I-Ib-11 | H | tert-butyl |
| I-Ib-12 | H | sec-butyl |
| I-Ib-13 | H | methoxy |
| I-Ib-14 | H | ethoxy |
| I-Ib-15 | H | methylthio |
| I-Ib-16 | H | trifluoromethyl |
| I-Ib-17 | chloro | H |
| I-Ib-18 | fluoro | H |
| I-Ib-19 | bromo | H |
| I-Ib-20 | methyl | H |
| I-Ib-21 | ethyl | H |
| I-Ib-22 | iso-propyl | H |
| I-Ib-23 | n-propyl | H |
| I-Ib-24 | n-butyl | H |
| I-Ib-25 | iso-butyl | H |
| I-Ib-26 | tert-butyl | H |

TABLE I-2-continued (I-Ib)

[Structure: thiophene ring with $R^{12}$ at 4-position, $R^{13}$ at 5-position, connected at 2-position to C(=N-O-COCH$_3$)-C(=O)-NH-CH$_2$CH$_2$-phenyl(3,4-diOCH$_3$)]

| Compound No. | $R^{12}$ | $R^{13}$ |
| --- | --- | --- |
| I-Ib-27 | sec-butyl | H |
| I-Ib-28 | methoxy | H |
| I-Ib-29 | ethoxy | H |
| I-Ib-30 | methylthio | H |
| I-Ib-31 | trifluoromethyl | H |
| I-Ib-32 | chloro | chloro |
| I-Ib-33 | fluoro | fluoro |
| I-Ib-34 | bromo | bromo |
| I-Ib-35 | methyl | methyl |
| I-Ib-36 | ethyl | ethyl |
| I-Ib-37 | methoxy | methoxy |
| I-Ib-38 | trifluoromethyl | trifluoromethyl |
| I-Ib-39 | chloro | methyl |
| I-Ib-40 | methyl | chloro |

TABLE I-3

(I-Ic)

[Structure: furan ring with $R^{12}$ at 4-position, $R^{13}$ at 5-position, connected at 2-position to C(=N-O-COCH$_3$)-C(=O)-NH-CH$_2$CH$_2$-phenyl(3,4-diOCH$_3$)]

where $R^{12}$ and $R^{13}$ represent the substituents mentioned in Table I-2.

TABLE I-4

(I-Id)

[Structure: $R^1$-C(=N-O-COCH$_3$)-C(=O)-NH-CH$_2$CH$_2$-phenyl(3,4-diOCH$_3$)]

| Compound No. | $R^1$ |
| --- | --- |
| I-Id-1 | 2-naphthyl |
| I-Id-2 | 2-benzofuranyl |
| I-Id-3 | 2-benzothienyl |

Table I-5
Compounds I-Ia-1 to I-Id-3 corresponding to the formulae I-Ia, I-Ib, I-Ic and I-Id, where a phenyl radical carrying the substituents given as $R^{10}$ and $R^{11}$, respectively, in the compounds I-Ia-1 to I-Ia-70 is replacing the 3,4-dimethoxyphenyl group (generally denoted as $R^4$).

Table I-6
Compounds I-Ia-1 to I-Id-3 corresponding to the formulae I-Ia, I-Ib, I-Ic and I-Id, where one of the following trisubstituted phenyl radicals is replacing the 3,4-dimethoxyphenyl group (generally denoted as $R^4$) 3,4,5-trimethoxyphenyl; 3,4,5-trichlorophenyl; 3,4,5-trimethylphenyl.

Table I-7
Compounds I-Ia-1 to I-Id-3 corresponding to the formulae I-Ia, I-Ib, Ic and I-Id, where a methoxycarbonyl group is replacing the acetyl group (generally denoted as $R^2$).

Furthermore, it has been found that the novel acyglyoxylic acid oximes of the general formula (I-I) are obtained when glyoxylic acid oximes of the formula (I-II)

(I-II)

[Structure: $R^1$-C(=N-OH)-C(=Q)-N($R^3$)-A-$R^4$]

in which
A, $R^1$, $R^3$ and $R^4$ are each as defined above are reacted with an activated acid derivative of one of the formulae (I-IV) to (I-X), (I-III)

[Structure: X-C(=Q$^1$)-$R^5$]

(I-IV)

[Structure: $R^5$-C(=O)-O-C(=O)-$R^5$]

(I-V)

[Structure: Cl-C(=O)-Q$^2$-$R^6$]

(I-VI)

[Structure: Alk-S-C(=S)-O-$R^6$]

(I-VII)

[Structure: $R^6$-S-C(=S)-S-$R^6$]

(I-VIII)

[Structure: X-C(=Q$^1$)-N($R^7$)($R^8$)]

(I-IX)

$R^7$—N=C=O (I-X)

$R^9$—SO$_2$Cl in which
$R^5$, $R^6$, $R^7$, $R^8$ and $R^9$ are each as defined above,
if appropriate in the presence of a diluent and if appropriate in the presence of a base.

The formula (I-II) provides a general definition of the glyoxylic acid oximes required as starting materials for carrying out the process according to the invention for preparing the compounds of the formula (I-I) according to the invention. In this formula (I-II), A, $R^1$, $R^3$ and $R^4$ each preferably in particular have those meanings which have already been mentioned in connection with the description of the compounds of the formula (I-I) according to the invention as being preferred and as being particularly preferred, respectively, for A, $R^1$, $R^3$ and $R^4$.

The starting materials of the formula (I-II) are obtained when carboxylic acid derivatives of the general formula (I-XI)

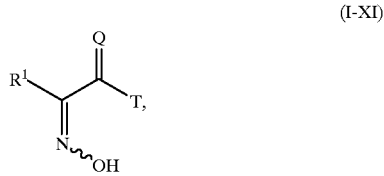

(I-XI)

in which
$R^1$ and Q are each as defined above and
T represents hydroxyl, halogen or alkoxy,
are reacted with an amine of the general formula (I-XII)

(I-XII)

in which
$R^3$, $R^4$ and A are each as defined above
or with a hydrohalide thereof,
if appropriate in the presence of an acid acceptor, such as, for example, triethylamine, if appropriate in the presence of a condensing agent, such as, for example, dicyclohexylcarbodiimide, and if appropriate in the presence of a diluent, such as, for example, toluene.

The formula (I-XI) provides a general definition of the carboxylic acid derivatives required as starting materials for preparing the glyoxylic acid oximes of the formula (I-II). In this formula (I-XI), Q and $R^1$ each preferably and in particular have those meanings which have already been mentioned in connection with the description of the compounds of the formula (I-I) according to the invention as being preferred and as being particularly preferred, respectively, for Q and $R^1$; T preferably represents alkoxy having 1 to 4 carbon atoms, in particular methoxy or ethoxy, represents hydroxyl or chlorine.

The starting materials of the formula (I-XI) are known and/or can be prepared by processes which are known per se (cf EP-A 178 826, EP-A 242 081, EP-A 382 375, EP-A 493 711, EP-A 432 503, DE-A 3 938 054).

The formula (I-XII) provides a general definition of the amines furthermore required as starting materials for preparing the glyoxylic acid oximes of the formula (I-II). In this formula (I-XII), $R^3$, $R^4$ and A each preferably and in particular have those meanings which have already been mentioned in connection with the description of the compounds of the formula (I-I) according to the invention as being preferred and as being particularly preferred, respectively, for $R^3$, $R^4$ and A.

The amines of the formula (I-XII) are known organic chemicals for synthesis and/or can be prepared by processes which are known per se.

The formulae (I-IV) to (I-X) provide general definitions of the activated acid derivatives furthermore required for carrying out the process according to the invention for preparing the compounds of the formula (I-I) according to the invention. In these formulae (I-IV) to (I-X), $R^5$, $R^6$, $R^7$, $R^8$ and $R^9$ each preferably and in particular have those meanings which have already been mentioned in connection with the description of the compounds of the formula (X-I) according to the invention as being preferred and as being particularly preferred, respectively, for $R^5$, $R^6$, $R^7$, $R^8$ and $R^9$.

The activated acid derivatives of the formulae (I-IV) to (I-X) are known organic chemicals for synthesis and/or can be prepared by processes which are known per se.

Suitable diluents for carrying out the process according to the invention for preparing the compounds of the formula (I-I) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane tetrahydrofuran, 1,2-dimethoxyethane, 1,2-diethoxyethane or anisole; ketones, such as acetone, butanone, methyl isobutyl ketone or cyclohexanone; nitrites, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; or sulphones, such as sulpholane.

The process according to the invention for preparing the compounds of the formula (I-I) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention for preparing the compounds of the formula (I-I) according to the invention, the reaction temperatures can be varied within a relatively wide range. In general, the process is carried out at temperatures of from −30° C. to 150° C., preferably at temperatures of from −10° C. to 80° C.

For carrying out the process according to the invention for preparing the compounds of the formula (I-I), generally 1 to 15 mol, preferably 2 to 8 mol, of activated acid derivative of one of the formulae (I-IV) to (I-X) are employed per mole of the glyoxylic acid oxime of the formula (I-II).

The process according to the invention for preparing the compounds of the formula (I-I) according to the invention is generally carried out under atmospheric pressure. However, it is also possible to operate under elevated or reduced pressure—generally between 0.1 bar and 10 bar.

The practice of the invention and the work-up and isolation of the reaction products are carried out by known processes (compare also the Preparation Examples).

Preference is also given to compounds of the general formula (II-I)

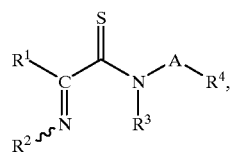

(II-I)

in which
A represents a single bond or optionally substituted alkylene,
$R^1$ represents cycloalkyl, cycloalkenyl, aryl or heterocyclyl, each of which is optionally substituted,
$R^2$ represents hydroxyl, amino, or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted,
$R^3$ represents hydrogen or represents alkyl, alkenyl, alkinyl or cycloalkyl, each of which is optionally substituted,
$R^4$ represents cycloalkyl, cycloalkenyl, aryl or heterocyclyl, each of which is optionally substituted.

The invention preferably provides compounds of the formula (II-I) in which
A represents a single bond or represents alkylene having 1 to 6 carbon atoms which is optionally mono- or polysubstituted by identical or different substituents, the possible substituents preferably being selected from the list below:
halogen, cyano, nitro, amino, hydroxyl, formyl, carboxyl, carbamoyl, thiocarbamoyl;
alkoxy, alkylthio, alkylsulphinyl or alkylsulphonyl having in each case 1 to 6 carbon atoms and being in each case straight-chain or branched;
alkenyl or alkenyloxy having in each case 2-to 6 carbon atoms and being in each case straight-chain or branched;
halogenoalkoxy, halogenoalkylthio, halogenolalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
cycloalkyl having 3 to 6 carbon atoms;
and also aryl or heterocyclyl, each of which is optionally mono- or polysubstituted by identical or different substituents selected from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms
and straight-chain or branched alkoxy or alkylthio having 1 to 4 carbon atoms
and straight-chain or branched halogenoalkoxy or halogenoalkylthio having 1 to 4 carbon atoms and 1 to 9 identical or different halogen atoms
and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms
and straight-chain or branched halogenoalkyl having 1 to 4 carbon atoms and 1 to 9 identical or different halogen atoms,
$R^1$ represents aryl, cycloalkyl or cycloalkenyl having 3 to 7 carbon atoms, or heterocyclyl having 3 to 12 ring members, each of which is optionally mono- or polysubstituted by identical or different substituents, the possible substituents preferably being selected from the list below:
halogen, cyano, nitro, amino, hydroxyl, formyl, carboxyl, carbamoyl, thiocarbamoyl;
alkyl, alkoxy, alkylthio, alkylsulphinyl or alkylsulphonyl having in each case 1 to 8 carbon atoms and being in each case straight-chain or branched;
alkenyl or alkenyloxy having in each case 2 to 6 carbon atoms and being in each case straight-chain or branched;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 8 carbon atoms in the individual alkyl moieties and being in each case straight-chain or branched;
alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms;
and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of
halogen, cyano and straight-chain or branched alkyl having 1 to 4 carbon atoms
and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms, $R^2$ represents hydroxyl, amino or represents alkyl, alkenyl, alkinyl, alkoxy, alkenyloxy, alkinyloxy, alkylamino, dialkylamino having in each case 1 to 4 carbon atoms in the respective alkyl moieties and being in each case optionally substituted by halogen, cyano or $C_1$–$C_4$-alkoxy, represents cycloalkyl, cycloalkenyl, cycloalkoxy, cycloalkenyloxy, cycloalkylamino, having 3 to 8 carbon atoms in the respective rings and being in each case in each case optionally substituted by halogen, cyano or $C_1$–$C_4$-alkoxy, or represents in each case optionally substituted phenyl, benzyl, benzyloxy, naphthyl, phenylamino or heterocyclyl having 3 to 8 ring members, the possible substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

or cycloalkyl having 3 to 6 carbon atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

The invention relates in particular to compounds of the formula (II-I), in which A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), optionally mono- or polysubstituted by identical or different substituents selected from the group consisting of fluorine, chlorine, cyano, methoxy, $R^1$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl;

cyclopropyl, cyclobutyl, cyclopentyl or cyclohexyl;

phenyl, benzyl, phenoxy, benzyloxy, optionally substituted by the abovementioned substituents, $R^2$ represents hydroxyl, amino or represents methyl, ethyl, n- or i-propyl, n-, i-, s- or t-butyl, vinyl, allyl, propargyl, methoxy, ethoxy, allyloxy, propargyloxy, methylamino, ethylamino, dimethylamino, each of which is optionally substituted by halogen, cyano, methoxy or ethoxy, represents cyclopropyl, cyclobutyl, cyclopentyl, cyclohexyl, cyclopentyloxy, cyclohexyloxy, cyclopentylamino, cyclohexylamino, each of which is optionally substituted by halogen, cyano, methoxy or ethoxy, or represents phenyl, benzyl, benzyloxy, naphthyl, phenylamino or heterocyclyl having 3 to 8 ring members and being in each case optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, ammo, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (II-I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), optionally mono- or polysubstituted by identical or different substituents selected from the group consisting of fluorine, chlorine, cyano, methoxy, $R^1$ represents cyclobutyl cyclopentyl or cyclohexyl, each of which is optionally mono- to hexasubstituted, preferred substituents being those mentioned below;

represents phenyl, naphthyl, furyl, benzofuranyl thienyl, benzothienyl, pyridyl, quinolyl, tetrahydrofuryl or perhydropyranyl, each of which is optionally mono- to trisubstituted, the possible substituents preferably being selected from the list below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl; cyclopropyl, cyclopentyl, cyclohexyl; phenyl, phenoxy, benzyloxy, optionally substituted by the abovementioned substituents;

$R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl cyclopropyl, cyclobutyl, cyclopentyl or cyclohexyl, $R^3$ represents hydrogen or represents methyl, $R^4$ represents cyclopropyl, cyclobutyl, cyclopentyl or cyclohexyl, each of which is optionally mono- to hexasubstituted, preferred substituents being those mentioned below, represents phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

A very particularly preferred group of compounds according to the invention are those compounds of the formula (II-I) in which A represents a single bond or represents methylene, 1,1-ethylene, 1,2-ethylene, 1,1-propylene, 1,2-propylene, 1,3-propylene or 2,2-propylene, $R^1$ represents thienyl, furanyl or phenyl which is optionally mono- or disubstituted by bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio or represents phenyl which is substituted by 3,4-methylene- and ethylenedioxo, propane-1,3-diyl and butane-1,4-diyl, each of which is optionally substituted by fluorine, or represents naphthyl, benzofuranyl or benzothienyl, $R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinoethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

Of very particular interest are compounds of the formula (II-I) in which the radical $R^1$ represents phenyl which is unsubstituted or substituted in position 3 and/or 4, or represents thienyl or furanyl which is unsubstituted or substituted in position 4 and/or 5, selected substituents being those mentioned above and in particular chlorine, bromine, fluorine, nitro, methylsulphonyl, phenyl, phenoxy, benzyloxy, cyclopropyl, cyclohexyl, methyl, ethyl, n-, i-propyl, n-, i-, s-, t-butyl, n-pentyl, n-hexyl, n heptyl, methoxy, ethoxy, methylthio, trifluoromethyl and trifluoromethoxy or phenyl which is substituted by 3,4-methylene- and ethylenedioxo, propane-1,3-diyl and butane-1,4-diyl, each of which is optionally substituted by fluorine, or benzofuranyl, benzothienyl or naphthyl which is substituted in position 2.

Particular preference is also given to compounds of the formula (II-I) in which
$R^2$ represents methoxy or ethoxy.

Particular preference is also given to compounds of the formula (II-I) in which
$R^2$ represents methylamino or ethylamino.

Particular preference is also given to compounds of the formula (II-I) in which
$R^3$ represents hydrogen.

Particular preference is also given to compounds of the formula (II-I) in which $R^4$ represents phenyl which is substituted by methoxy in position 3 and 4.

In a group of compounds which is likewise particularly preferred, A represents —CH$_2$—CH$_2$—.

The radical definitions given above as general or as being preferred apply both to the end products of the formula (II-I) and also, correspondingly, to the starting materials and intermediates required in each case for the preparation.

These radical definitions can be combined with one another at will, i.e. including combinations between the given ranges of preferred compounds.

Preferred individual compounds are shown in the tables below:

TABLE II-1

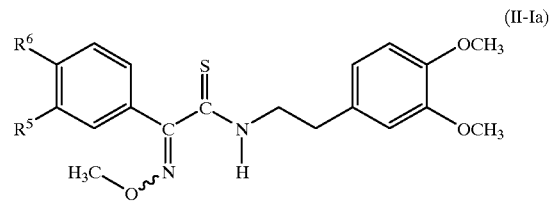

(II-Ia)

| Compound No. | $R^5$ | $R^6$ |
|---|---|---|
| II-Ia-1 | H | H |
| II-Ia-2 | H | chloro |
| II-Ia-3 | H | fluoro |
| II-Ia-4 | H | bromo |
| II-Ia-5 | H | methyl |
| II-Ia-6 | H | ethyl |
| II-Ia-7 | H | iso-propyl |
| II-Ia-8 | H | n-propyl |
| II-Ia-9 | H | n-butyl |
| II-Ia-10 | H | iso-butyl |
| II-Ia-11 | H | tert-butyl |
| II-Ia-12 | H | sec-butyl |
| II-Ia-13 | H | methoxy |
| II-Ia-14 | H | ethoxy |
| II-Ia-15 | H | methylthio |
| II-Ia-16 | H | trifluoromethyl |
| II-Ia-17 | chloro | H |
| II-Ia-18 | fluoro | H |
| II-Ia-19 | bromo | H |
| II-Ia-20 | methyl | H |
| II-Ia-21 | ethyl | H |
| II-Ia-22 | iso-propyl | H |
| II-Ia-23 | n-propyl | H |
| II-Ia-24 | n-butyl | H |
| II-Ia-25 | iso-butyl | H |
| II-Ia-26 | tert-butyl | H |
| II-Ia-27 | sec-butyl | H |
| II-Ia-28 | methoxy | H |
| II-Ia-29 | ethoxy | H |
| II-Ia-30 | methylthio | H |

TABLE II-1-continued (II-Ia)

Structure: R6, R5 substituted phenyl connected to C(=S)NH-CH2CH2-(3,4-dimethoxyphenyl), with =N-OCH3 group

| Compound No. | R⁵ | R⁶ |
|---|---|---|
| II-Ia-31 | trifluoromethyl | H |
| II-Ia-32 | chloro | chloro |
| II-Ia-33 | fluoro | fluoro |
| II-Ia-34 | bromo | bromo |
| II-Ia-35 | methyl | methyl |
| II-Ia-36 | ethyl | ethyl |
| II-Ia-37 | —OCH₂O— | |
| II-Ia-38 | —OCH₂CH₂O— | |
| II-Ia-39 | —OCF₂O— | |
| II-Ia-40 | —OCF₂CF₂O— | |
| II-Ia-41 | —(CH₂)₃— | |
| II-Ia-42 | —(CH₂)₄— | |
| II-Ia-43 | methoxy | methoxy |
| II-Ia-44 | ethoxy | ethoxy |
| II-Ia-45 | methylthio | methylthio |
| II-Ia-46 | trifluoromethyl | trifluoromethyl |
| II-Ia-47 | chloro | methyl |
| II-Ia-48 | methyl | chloro |
| II-Ia-49 | chloro | methoxy |
| II-Ia-50 | methoxy | chloro |
| II-Ia-51 | chloro | ethyl |
| II-Ia-52 | ethyl | chloro |
| II-Ia-53 | methoxy | ethoxy |
| II-Ia-54 | ethoxy | methoxy |
| II-Ia-55 | methyl | methoxy |
| II-Ia-56 | methoxy | methyl |
| II-Ia-57 | methyl | ethyl |
| II-Ia-58 | ethyl | methyl |
| II-Ia-59 | methoxy | ethyl |
| II-Ia-60 | ethyl | methoxy |
| II-Ia-61 | H | nitro |
| II-Ia-62 | H | methylsulphonyl |
| II-Ia-63 | H | phenoxy |
| II-Ia-64 | H | phenyl |
| II-Ia-65 | H | benzyloxy |
| II-Ia-66 | H | pentyl |
| II-Ia-67 | H | hexyl |
| II-Ia-68 | H | heptyl |
| II-Ia-69 | H | cyclopropyl |
| II-Ia-70 | H | cyclohexyl |

TABLE II-2

(II-Ib)

Structure: R7, R8 substituted thiophene connected to C(=S)NH-CH2CH2-(3,4-dimethoxyphenyl), with =N-OCH3 group

| Compound No. | R⁷ | R⁸ |
|---|---|---|
| II-Ib-1 | H | H |
| II-Ib-2 | H | chloro |
| II-Ib-3 | H | fluoro |
| II-Ib-4 | H | bromo |
| II-Ib-5 | H | methyl |
| II-Ib-6 | H | ethyl |

TABLE II-2-continued (II-Ib)

| Compound No. | R⁷ | R⁸ |
|---|---|---|
| II-Ib-7 | H | iso-propyl |
| II-Ib-8 | H | n-propyl |
| II-Ib-9 | H | n-butyl |
| II-Ib-10 | H | iso-butyl |
| II-Ib-11 | H | tert-butyl |
| II-Ib-12 | H | sec-butyl |
| II-Ib-13 | H | methoxy |
| II-Ib-14 | H | ethoxy |
| II-Ib-15 | H | methylthio |
| II-Ib-16 | H | trifluoromethyl |
| II-Ib-17 | chloro | H |
| II-Ib-18 | fluoro | H |
| II-Ib-19 | bromo | H |
| II-Ib-20 | methyl | H |
| II-Ib-21 | ethyl | H |
| II-Ib-22 | iso-propyl | H |
| II-Ib-23 | n-propyl | H |
| II-Ib-24 | n-butyl | H |
| II-Ib-25 | iso-butyl | H |
| II-Ib-26 | tert-butyl | H |
| II-Ib-27 | sec-butyl | H |
| II-Ib-28 | methoxy | H |
| II-Ib-29 | ethoxy | H |
| II-Ib-30 | methylthio | H |
| II-Ib-31 | trifluoromethyl | H |
| II-Ib-32 | chloro | chloro |
| II-Ib-33 | fluoro | fluoro |
| II-Ib-34 | bromo | bromo |
| II-Ib-35 | methyl | methyl |
| II-Ib-36 | ethyl | ethyl |
| II-Ib-37 | methoxy | methoxy |
| II-Ib-38 | trifluoromethyl | trifluoromethyl |
| II-Ib-39 | chloro | methyl |
| II-Ib-40 | methyl | chloro |

TABLE II-3

(II-Ic)

Structure: R7, R8 substituted furan connected to C(=S)NH-CH2CH2-(3,4-dimethoxyphenyl), with =N-OCH3 group where $R^7$ and $R^8$ each represent the substituents mentioned in Table 11-2.

TABLE II-4

(II-Id)

| Compound No. | R¹ |
|---|---|
| II-Id-1 | 2-naphthyl |
| II-Id-2 | 2-benzofuranyl |
| II-Id-3 | 2-benzothienyl |

Table II-5

Compounds II-Ia-1 to II-Id-3 corresponding to the formulae III-Ia, II-Ib, II-Ic and II-Id, where a phenyl radical carrying the substituents given as $R^5$ and $R^6$, respectively, in the compounds II-Ia-1 to II-Ia-3 is replacing the 3,4-dimethoxyphenyl group (generally denoted as $R^4$).

Table II-6

Compounds II-Ia-1 to II-Id-3 corresponding to the formulae II-Ia, II-Ib, II-Ic and II-Id, where one of the following trisubstituted phenyl radicals is replacing the 3,4-dimethoxyphenyl group (generally denoted as $R^4$): 3,4,5-trimethoxyphenyl; 3,4,5-trichlorophenyl; 3,4,5-trimethylphenyl.

Table II-7

Compounds II-Ia-1 to II-Id-3 corresponding to the formulae II-Ia, II-Ib, II-Ic and II-Id, where a methylamino group is replacing the methoxy group (generally denoted as $R^2$).

Furthermore, it has been found that the novel glyoxylic acid thioamides of the general formula (II-I) are obtained when glyoxylic acid amides of the general formula (II-II)

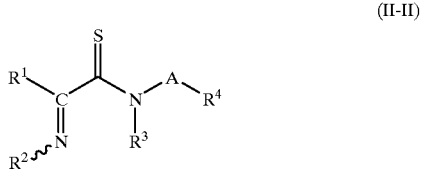

(II-II)

in which

A, $R^1$, $R^2$, $R^3$ and $R^4$ are each as defined above are reacted with a sulphurizing agent, if appropriate in the presence of a diluent.

The formula (II-II) provides a general definition of the glyoxylic acid amides required as staring materials for carrying out the process according to the invention for preparing the compounds of the formula (II-I) according to the invention. In this formula (II-II), A, $R^1$, $R^2$, $R^3$ and $R^4$ each preferably in particular have those meanings which have already been mentioned in connection with the description of the compounds of the formula (II-I) according to the invention as being preferred and as being particularly preferred, respectively, for A, $R^1$, $R^2$, $R^3$ and $R^4$.

The glyoxylic acid amides of the general formula (II-II) are obtained when carboxylic acid derivatives of the general formula (II-III)

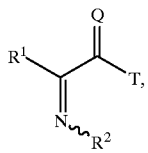

(II-III)

in which
$R^1$ and $R^2$ are each as defined above and
T represents hydroxyl, halogen or alkoxy
are reacted with an amine of the general formula (II-IV)

$$HN\!-\!A\!-\!R^4,$$ (II-IV)
(with $R^3$ on N)

in which
$R^3$, $R^4$ and A are each as defined above
or with a hydrohalide thereof
if appropriate in the presence of an acid acceptor, such as, for example, triethylamine, if appropriate in the presence of a condensing agent, such as, for example, a chloroformate, and if appropriate in the presence of a diluent, such as, for example, dichloromethane.

The formula (II-III) provides a general definition of the carboxylic acid derivatives required as starting materials for preparing the glyoxylic acid amides of the formula (II-II). In this formula (II-III), $R^1$ and $R^2$ preferably in particular have those meanings which have already been mentioned in connection with the description of the compounds of the formula (II-I) according to the invention as being preferred and as being particularly preferred, respectively, for $R^1$ and $R^2$; T preferably represents alkoxy having 1 to 4 carbon atoms, in particular methoxy or ethoxy, represents hydroxyl or chlorine.

The starting materials of the formula (II-III) are known and/or can be prepared by processes which are known per se (cf EP-A 178 826, EP-A 242 081, EP-A 382 375, EP-A 493 711, EP-A 432 503, DE-A 3 938 054, J. Heterocycl. Chem. (1990), 27(3), 487–95, Farmaco, Ed. Sci. (1980), 35(5), 394–404, Justus Liebigs Ann. Chem. (1969), 722, 3844, Justus Liebigs Anm. Chem (1969), 722, 29–37, Tetrahedron 1971, 3431–6).

The formula (II-IV) provides a general definition of the amines further to be used as starting materials for preparing the glyoxylic acid amides of the formula (II-II). In this formula (II-IV), A, $R^3$ and $R^4$ each preferably in particular have those meanings which have already been mentioned in connection with the description of the compounds of the formula (II-I) according to the invention as being preferred and as being particularly preferred, respectively, for A, $R^3$ and $R^4$.

The starting materials of the formula (II-IV) are known organic chemicals for synthesis and/or can be prepared by processes which are known per se.

Suitable sulphurizing agents for carrying out the process according to the invention for preparing the compounds of the formula (II-I) according to the invention are all reagents which are capable of exchanging oxygen atoms which are attached to carbon in a molecule for sulphur atoms, such as, for example, hydrogen sulphide, phosphorus pentasulphide or Lawesson's Reagent.

Suitable diluents for carrying out the process according to the invention for preparing the compounds of the formula (II-I) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; amides, such as NN-dimethylformamide, N,N-dimethylacetamide, N-methylformanilide, N-methylpyrrolidone or hexamethylphosphoric triamide; sulphoxides, such as dimethyl sulphoxide; sulphones, such as sulpholane.

When carrying out the process according to the invention for preparing the compounds of the formula (II-I) according to the invention, the reaction temperatures can be varied within a relatively wide range. In general, the reaction is carried out at temperatures of from 0° C. to 150° C., preferably at temperatures of from 0° C. to 80° C.

For carrying out the process according to the invention for preparing the compounds of the formula (II-I), generally 0.1 to 15 mol, preferably 0.5 to 8 mol, of sulphurizing agent are employed per mole of the glyoxylic acid amide of the formula (I-II).

Preference is also given to compounds of the general formula (III-I)

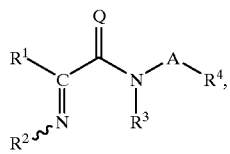

in which
A represents a single bond or optionally substituted alkylene,
Q represents oxygen or sulphur,
$R^1$ represents optionally substituted benzoheterocyclyl which is attached on the benzene ring and has one, two or three heteroatoms (but at most one heteroatom representing oxygen),
$R^2$ represents hydroxyl, amino or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted, or represents one of the groupings below:

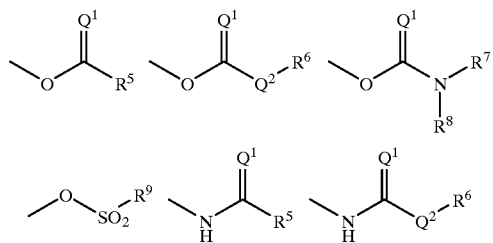

in which
$Q^1$ and $Q^2$ independently of one another each represent oxygen or sulphur,
$R^5$ represents hydrogen or optionally substituted alkyl or aryl,
$R^6$ represents optionally substituted alkyl or ar yl,
$R^7$ represents hydrogen or optionally substituted alkyl or aryl,
$R^8$ represents optionally substituted alkyl or aryl, or
$R^7$ and $R^8$ together with the linking nitrogen atom represent an optionally alkyl-substituted heterocyclic ring,
$R^9$ represents optionally substituted alkyl, dialkylamino, saturated heterocyclyl which is attached via nitrogen or aryl,
$R^3$ represents hydrogen or represents alkyl, alkenyl, alkinyl or cycloalkyl, each of which is optionally substituted,
$R^4$ represents cycloalkyl, cycloalkenyl, aryl or heterocyclyl, each of which is optionally substituted.

The invention preferably provides compounds of the formula (III-I) in which
A represents a single bond or represents alkylene having 1 to 6 carbon atoms which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

cycloalkyl having 3 to 6 carbon atoms;

and also aryl or heterocyclyl, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms, Q represents oxygen or sulphur, $R^1$ represents benzoheterocyclyl having 3 to 12 ring members in the heterocyclyl moiety and one, two or three heteroatoms (but at most one heteroatom representing oxygen) which is attached on the benzene ring and is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 8 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 8 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched allyl having 1 to 4 carbon atoms and straight-chain or branched halogenoalkyl having 1 to 4 carbon atoms and 1 to 9 identical or different halogen atoms.

$R^2$ represents hydroxyl, amino or represents alkyl, alkenyl, alkinyl, alkoxy, alkenyloxy, alkinyloxy, alkylamino, dialkylamino having in each case 1 to 4 carbon atoms in the respective alkyl moieties and being in each case optionally substituted by halogen, cyano or $C_1-C_4$-alkoxy, represents cycloalkyl cycloalkenyl, cycloalkoxy, cycloalkenyloxy, cycloalkylamino, having 3 to 8 carbon atoms in the respective rings and being in each case optionally substituted by halogen, cyano or $C_1-C_4$-alkoxy, or represents in each case optionally substituted phenyl, benzyl, benzyloxy, naphthyl, phenylamino or heterocyclyl having 3 to 8 ring members, the possible substituents preferably being selected from the list below:

halogen, cyano, nitro, amino, hydroxyl, formyl, carboxyl, carbamoyl, thiocarbamoyl;

alkyl alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms, or $R^2$ represents one of the groupings below:

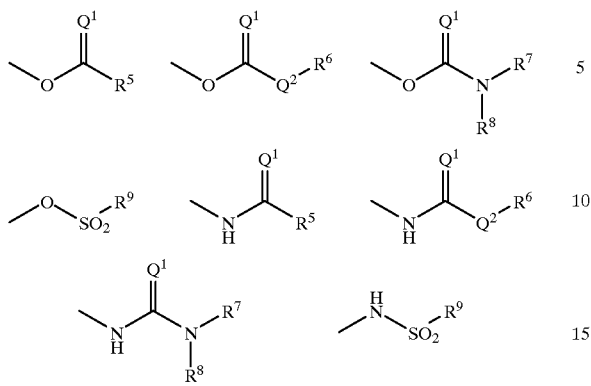

in which $Q^1$ and $Q^2$ independently of one another each represent oxygen or sulphur, $R^5$ represents hydrogen or alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^6$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^7$ represents hydrogen, alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^8$ represents allyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, or $R^7$ and $R^8$ together with the linking nitrogen atom represent an optionally methyl-substituted heterocyclic ring, $R^9$ represents allyl having 1 to 6 carbon atoms, dialkylamino having in each case 1 to 4 carbon atoms in the individual alkyl moieties, heterocyclyl having 3 to 7 ring members which is attached via nitrogen or represents aryl or arylalkyl having 1 to 4 carbon atoms in the alkyl moiety, each of which is optionally substituted in the aryl moiety by halogen, cyano, nitro, allyl or alkoxy having in each case 1 to 4 carbon atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the possible a substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and allylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to identical or different halogen atoms.

The invention relates in particular to compounds of the formula (III-I) in which A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-2-methyl-propylene), each of which is optionally mono- or polysubstituted by identical or different substituents selected from the group consisting of fluorine, chlorine, cyano and methoxy, Q represents oxygen or sulphur, $R^1$ represents one of the groupings below

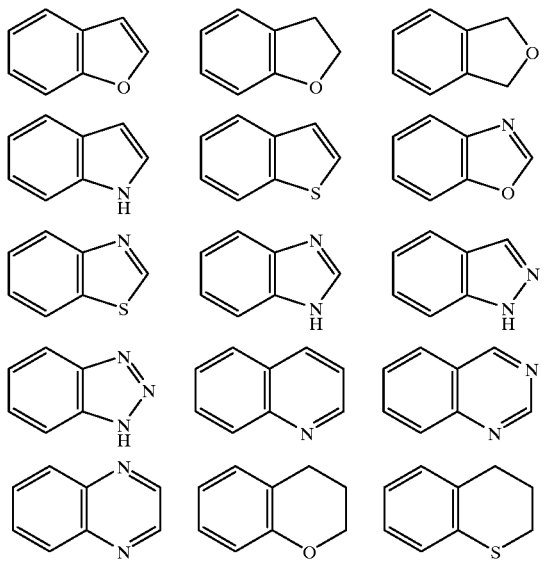

each of which is attached via a carbon atom of the respective benzene ring and each of which may be optionally mono- to trisubstituted by identical or different substituents from the substituents listed below.

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

trimethylene (propane-1,3-diyl), tetramethylene (butane-1,4diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl;

cyclopropyl, cyclobutyl, cyclopentyl or cyclohexyl;

bentyl, phenoxy, benzyloxy or phenyl which is optionally substituted by the abovementioned substituents, $R^2$ represents hydroxyl, amino or represents methyl, ethyl n- or i-propyl, f-, i-, s- or t-butyl, vinyl allyl, propargyl, methoxy, ethoxy, allyloxy, propargyloxy, methylamino, ethylamino, dimethylamino, each of which is optionally substituted by halogen, cyano, methoxy or ethoxy, represents cyclopropyl, cyclobutyl, cyclopentyl, cyclohexyl, cyclopentyloxy, cyclohexyloxy, cyclopentylamino, cyclohexylamino, each of which is optionally substituted by halogen, cyano, methoxy or ethoxy, or represents phenyl, benzyl, benzyloxy, naphthyl, phenylamino or heterocyclyl having 3 to 8 ring members, each of which is optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethythio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl, or $R^2$ represents one of the groupings below:

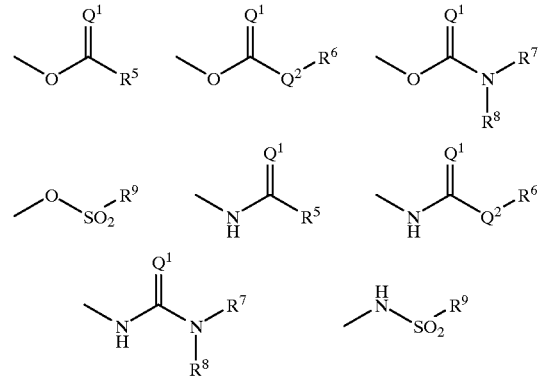

in which $Q^1$ and $Q^2$ independently of one another each represent oxygen or sulphur, $R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl,-propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (III-I) in which

A represents a single bond or represents methylene, 1,1-ethylene, 1,2-ethylene 1,1-, 1,2-, 1,3- or 2,2-propylene, 1,1-, 1,2-, 1,3-, 1,4,2,2-, 2,3-butylene or 1,1-, 1,2- or 1,3-(2-methyl-propylene), optionally mono- or polysubstituted by identical or different substituents selected from the group consisting of fluorine, chlorine, cyano, methoxy, Q represents oxygen or sulphur, $R^1$ represents one of the groupings below

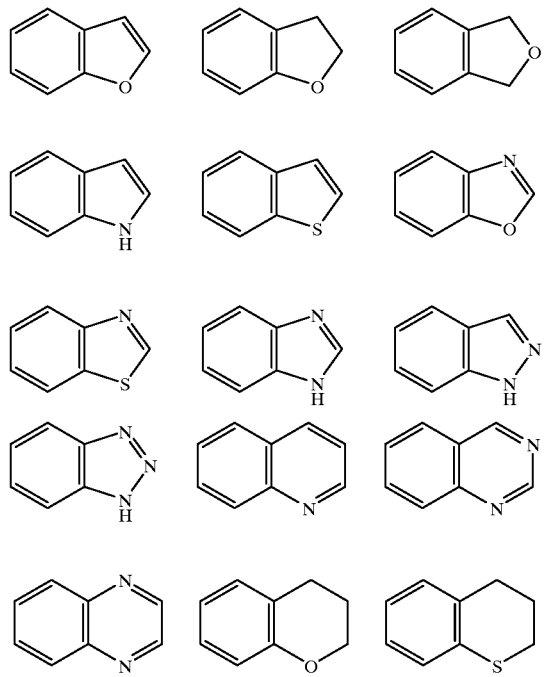

each of which is attached via a carbon atom of the respective benzene ring and each of which may be optionally mono- to trisubstituted by identical or different substituents from the substituents listed below:

fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl, trifluoromethylsulphonyl, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl;

trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl; cyclopropyl, cyclopentyl, cyclohexyl; phenoxy, benzyloxy, phenyl, which is optionally substituted by the abovementioned substituents;

$R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl, or $R^2$ represents one of the groupings below:

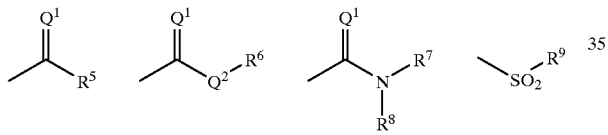

in which $Q^1$ and $Q^2$ independently of one another each represent oxygen or sulphur, $R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl, $R^4$ represents cyclopropyl, cyclobutyl, cyclopentyl or cyclohexyl, each of which is optionally mono- to hexasubstituted, preferred substituents being those mentioned below;

represents phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl ethoximinomethyl, methoximinoethyl or ethoximinoethyl, represents trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

A very particularly preferred group of compounds according to the invention are those compounds of the formula (III-I) in which A represents a single bond or represents methylene, 1,1-ethylene, 1,2-ethylene, 1,1 -propylene, 1,2-propylene, 1,3-propylene or 2,2-propylene, Q represents oxygen, $R^1$ represents one of the groupings below

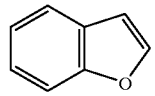 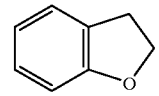 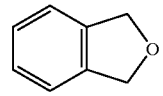

-continued

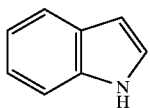
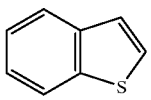
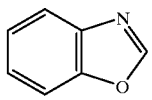

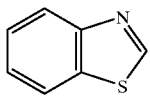
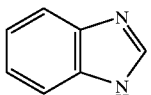
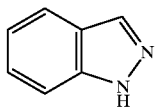

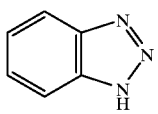
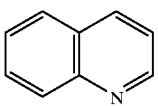
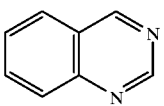

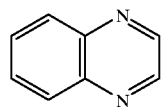
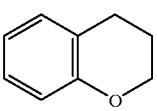
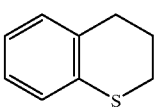

each of which is attached via a carbon atom of the respective benzene ring and each of which may be optionally mono- to trisubstituted by identical or different substituents from the substituents listed below:
bromine, chlorine, fluorine, nitro, methylsulphonyl, phenyl, phenyloxy, benzyloxy, cyclopropyl, cyclohexyl, methyl, ethyl, n- or i-propyl, n-, i-, s- or t-butyl, n-pentyl, n-hexyl, n-heptyl, methoxy, ethoxy, trifluoromethyl, trifluoromethoxy and/or methylthio, $R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the possible substituents preferably being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl,
trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, or $R^2$ represents one of the groupings below:

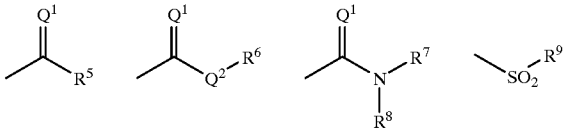

in which
$Q^1$ and $Q^2$ each represent oxygen,
$R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^6$ represents methyl, ethyl n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^7$ represents hydrogen, methyl, ethyl, n- or i-propyl, n-, i-, s- or t-butyl or represents phenyl, benzyl, 1-phenylethyl or 2-phenylethyl, each of which is optionally 'substituted in the phenyl moiety by fluorine, chlorine, bromine, cyano, nitro, methyl, ethyl, n- or i-propyl, n-, i-, s- or t-butyl, methoxy or ethoxy,
$R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, ;-, s- or t-butyl, methoxy or ethoxy, or
$R^7$ and $R^8$ together with the linking nitrogen atom represent an optionally methyl-substituted heterocyclic ring,
$R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^3$ represents hydrogen or methyl,
$R^4$ represents cyclohexyl or optionally mono- to trisubstituted phenyl, thienyl, furyl, benzofuryl, benzothienyl, pyridyl, pyrimidinyl, naphthyl, quinolyl, the possible substituents preferably being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

Particular preference is also given to compounds of the formula (III-I) in which $R^2$ represents methoxy, fluoromethoxy, ethoxy, methylamino or dimethylamino.

Particular preference is also given to compounds of the formula (III-I) in which $R^3$ represents hydrogen.

Particular preference is also given to compounds of the formula (III-I) in which $R^4$ represents phenyl which is substituted by methoxy in position 3 and 4.

In a further particularly preferred group of compounds A represents —CH$_2$—CH$_2$—.

The radical definitions given above as general or as being preferred apply both to the end products of the formula (III-I) and, correspondingly, to the starting materials and intermediates required in each case for the preparation.

These radical definitions can be combined with one another at will, i.e. including combinations between the given ranges of preferred compounds.

Furthermore, it has been found that the novel benzoheterocyclylglyoxylic acid amides of the general formula (II-I) are obtained when Process III-a) carboxylic acid derivatives of the general formula (III-II)

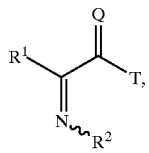

(III-II)

in which $R^1$, $R^2$ and Q are each as defined above and

T represents hydroxyl, halogen or alkoxy are reacted with an amine of the general formula (III-III)

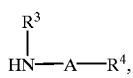

(III-III)

in which $R^3$, $R^4$ and A are each as defined above or with a hydrohalide thereof, if appropriate in the presence of an acid acceptor, if appropriate in the presence of a condensing agent and if appropriate in the presence of a diluent, or when Process III-b) glyoxylic acid amides of the general formula (III-IV)

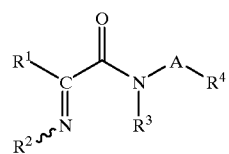

(III-IV)

in which

A, $R^1$, $R^2$, $R^3$ and $R^4$ are each as defined above are reacted with a sulphurizng agent, if appropriate in the presence of a diluent, or when Process III-c) glyoxylic acid derivatives of the formula (III-V)

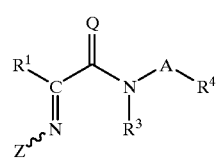

(III-V)

in which

A, $R^1$, $R^3$ and $R^4$ are each as defined above and

Z represents hydroxyl or amino, are reacted with an activated acid derivative of one of the formulae (III-VI) to (III-XII),

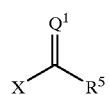

(III-VI)

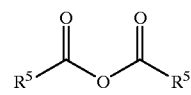

(III-VI)

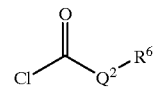

(III-VII)

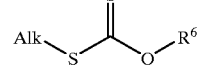

(III-VIII)

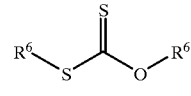

(III-IX)

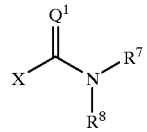

(III-X)

(III-XI)

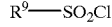

(III-XII)

in which $R^5$, $R^6$, $R^7$, $R^8$ and $R^9$ are each as defined above, if appropriate in the presence of a diluent and if appropriate in the presence of a base.

The formula (III-I) provides a general definition of the carboxylic acid derivatives required as starting materials for carrying out the process III-a) according to the invention. In this formula (III-II), Q and $R^1$ each preferably and in particular have those meanings which have already been mentioned in connection with the description of the compounds of the formula (III-I) according to the invention as being preferred and as being particularly preferred, respectively, for Q and $R^1$; T preferably represents alkoxy having 1 to 4 carbon atoms, in particular methoxy or ethoxy, represents hydroxyl or chlorine.

The starting materials of the formula (III-II) are known and/or can be prepared by processes which are known per se (cf. EP-A 178 826, EP-A 242 081, EP-A 382 375, EP-A 493 711, EP-A 432 503, DE-A 3 938 054, J. Heterocycl. Chem. (1990), 27(3), 487–95, Farmaco, Ed. Sci. (1980), 35(5), 394–404, Justus Liebigs Ann. Chem. (1969), 722, 3844, Justus Liebigs Ann. Chem. (1969), 722, 29–37, Tetrahedron 1971, 3431–6).

The formula (III-III) provides a general definition of the amines furthermore required as starting materials for carrying out the process III-a) according to the invention. In this formula (III-III), $R^3$, $R^4$ and A each preferably and in particular have those meanings which have already been mentioned in connection with the description of the compounds of the formula (III-I) according to the invention as being preferred and as being particularly preferred, respectively, for $R^3$, $R^4$ and A.

The amines of the formula (III-III) are known organic chemicals for synthesis and/or can be prepared by processes which are known per se.

The formula (III-IV) provides a general definition of the glyoxylic acid amides required as starting materials for carrying out the process III-b) according to the invention. In this formula (III-IV), A, $R^1$, $R^2$, $R^3$ and $R^4$ each preferably and in particular have those meanings which have already been mentioned in connection with the description of the compounds of the formula (III-I) according to the invention as being preferred and as being particularly preferred, respectively, for A, $R^1$, $R^2$, $R^3$ and $R^4$.

The glyoxylic acid amides of the general formula (II-IV) are compounds according to the invention and can be obtained by the processes III-a) or III-c) according to the invention.

Suitable sulphurizing agents for carrying out the process III-b) according to the invention are all reagents which are capable of exchanging oxygen atoms which are attached to carbon for sulphur atoms, such as, for example, hydrogen sulphide, phosphorus pentasulphide or Lawesson's Reagent The formula (III-V) provides a general definition of the glyoxylic acid derivatives required as starting materials for carrying out the process III-c) according to the invention. In this formula (II-V), A, $R^1$, $R^3$ and $R^4$ each preferably in particular have those meanings which have already been mentioned in connection with the description of the compounds of the formula (III-I) according to the invention as being preferred and as being particularly preferred, respectively, for A, $R^1$, $R^3$ and $R^4$. Z represents hydroxyl or amino.

The starting materials of the formula (III-V) are compounds according to the invention and can be obtained by the processes III-a) or III-b) according to the invention.

The formulae (III-VI) to (III-XII) provide general definitions of the activated acid derivatives furthermore required for carrying out the process III-c) according to the invention for preparing the compounds of the formula (III-I) according to the invention. In these formulae (III-VI) to (III-XII), $R^5$, $R^6$, $R^7$, $R^8$ and $R^9$ each preferably and in particular have those meanings which have already been mentioned in connection with the description of the compounds of the formula (III-I) according to the invention as being preferred and as being particularly preferred, respectively, for $R^5$, $R^6$, $R^7$, $R^8$ and $R^9$.

The activated acid derivatives of the formulae (III-VI) to (III-XII) are known organic chemicals for synthesis and/or can be prepared by processes which are known per se.

The process III-a) according to the invention is, if appropriate, carried out in the presence of a diluent. Suitable diluents for carrying out the process according to the invention are water and organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether, ketones, such as acetone, butanone or methyl isobutyl ketone; nitriles, such as acetonitrile, propionitrile or benzonitrile; amides, such as NN-dimethylformamide, N,N-dimethylacetamide, N-methylformanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether, diethylene glycol monoethyl ether, mixtures thereof with water or pure water.

The process III-a) according to the invention is, if appropriate, carried out in the presence of a suitable acid acceptor; Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N,N-dimethylaminopyridine, diazabicyclooctane (DABCO), diazabicyclononene (DBN) or diazabicycloundecene (DBU).

The process III-a) according to the invention is, if appropriate, carried out in the presence of a suitable condensing agent. Suitable condensing agents are all condensing agents which are customarily used for such amidation reactions. Examples which may be mentioned are acid halide formers such as phosgene, phosphorus tribromide, phosphorous trichloride, phosphorus pentachloride, phosphorus oxychloride or thionyl chloride; anhydride formers such as ethyl chloroformate, methyl chloroformate or methanesulphonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenyl phosphine/carbon tetrachloride.

The process III-a) according to the invention is, if appropriate, carried out in the presence of a catalyst.

Examples which may be mentioned are 4 trimethylaminopyridine, 1-hydroxy-benzotriazole or dimethylformamide.

When carrying out the process III-a) according to the invention, the reaction temperatures can be varied within a relatively wide range. In general, the reaction is carried out at temperatures between −20° C. and +200° C., preferably at temperatures between 0° C. and 150° C.

For carrying out the process III-a) according to the invention, generally 1 to 5 mol, preferably 1.0 to 2.5 mol, of amine are employed per mole of carboxylic acid derivative of the formula (III-II).

The practice of the reaction and the work-up and the isolation of the reaction products are carried by known processes (cf. the Preparation Examples).

The process III-a) according to the invention can also be carried out as a two-step process. The carboxylic acid derivatives of the general formula (III-II) are then initially converted into an activated form and, in a subsequent step, reacted with the amines of the general formula (III-III) to give the alkoximinoacetic acid derivatives of the general formula (III-I) according to the invention.

Suitable activated forms of the carboxylic acid derivatives of the formula (III-II) are all carboxy-activated derivatives, such as, for example, acyl halides, preferably acyl chlorides, acid azides, furthermore symmetric and mixed anhydrides, such as, for example, the mixed 0-alkylcarbonic anhydrides, furthermore activated esters, such as, for example, p-nitrophenyl esters or N-hydroxysuccinimide esters and also adducts with condensing agents, such as, for example, dicyclohexylcarbodiimide or in situ generated activated forms of the carboxylic acids.

Suitable diluents for carrying out the process III-b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole.

When carrying out the process III-b) according to the invention, the reaction temperatures can be varied within a relatively wide range. In general, the reaction is carried out at temperatures of from 0° C. to 150° C., preferably at temperatures of from 0° C. to 80° C.

For carrying out the process III-b) according to the invention for preparing the compounds of the formula (III-I), generally 0.1 to 15 mol, preferably 0.5 to 8 mol of sulphurizing agent are employed per mole of the glyoxylic acid amide of the formula (III-IV).

Suitable diluents for carrying out the process III-c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrole, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; or sulphones, such as sulpholane.

The process III-c) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process III-c) according to the invention, the reaction temperatures can be varied within a relatively wide range. In general, the reaction is carried out at temperatures of from 0° C. to 150° C., preferably at temperatures of from 0° C. to 80° C.

For carrying out the process III-c) according to the invention for preparing the compounds of the formula (III-I), generally 1 to 15 mol, preferably 2 to 8 mol, of activated acid derivative of one of the formulae (III-VI) to (III-XII) are employed per mole of the glyoxylic acid derivative of the formula (III-V).

Preference is also given to compounds of the general formula (IV-I),

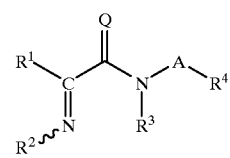

(IV-I)

in which

A represents a single bond or optionally substituted alkylene,

Q represents oxygen or sulphur, $R^1$ represents a tricycle

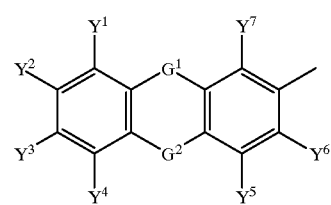

or

-continued

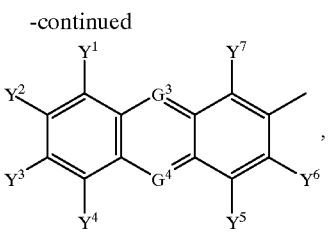

in which
G¹ and G² independently of one another each represent a single bond, alkanediyl, alkenediyl, oxygen, sulphur, —NH—, -N(alkyl)- or carbonyl,
G³ and G⁴ independently of one another each represent nitrogen or a grouping

and
Y¹, Y², Y³, Y⁴, Y⁵, Y⁶, Y⁷ and Y⁸ independently of one another each represent hydrogen, halogen, cyano, nitro, represent alkyl, alkoxy, alkylamino, dialkylamino, alkylthio, alkylsulphinyl alkylsulphonyl or cycloalkyl, each of which is optionally substituted, or
R² represents hydroxyl, amino or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted, or represents one of the groupings below:

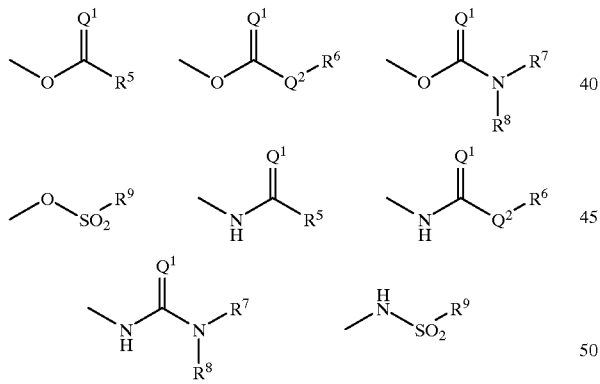

in which
Q¹ and Q² independently of one another each represent oxygen or sulphur,
R⁵ represents hydrogen or represents optionally substituted alkyl or aryl,
R⁶ represents optionally substituted alkyl or aryl,
R⁷ represents hydrogen or optionally substituted alkyl or aryl,
R⁸ represents optionally substituted alkyl or aryl, or
R⁷ and R⁸ together with the linking nitrogen atom represent an optionally alkyl-substituted heterocyclic ring,
R⁹ represents optionally substituted alkyl, dialkylamino, saturated heterocyclyl which is attached via nitrogen or aryl, R³ represents hydrogen or represents alkyl, alkenyl, alkinyl or cycloalkyl, each of which is optionally substituted,
R⁴ represents cycloalkyl, cycloalkenyl, aryl or heterocyclyl, each of which is optionally substituted.

The invention preferably provides compounds of the formula (IV-I) in which

A represents a single bond or represents alkylene having 1 to 6 carbon atoms which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

cycloalkyl having 3 to 6 carbon atoms;

and also aryl or heterocyclyl, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms, Q represents oxygen or sulphur,
R¹ represents a tricycle

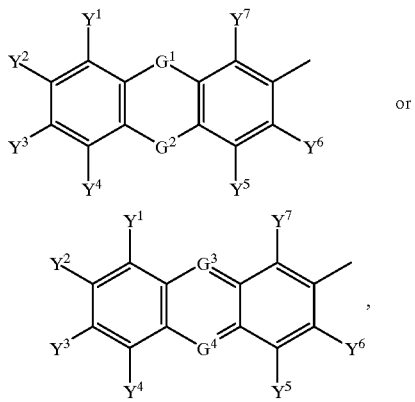

in which
G¹ and G² independently of one another each represent a single bond, alkanediyl, alkenediyl, oxygen, sulphur, —NH—, -N(alkyl)- or carbonyl
G³ and G⁴ independently of one another each represent nitrogen or a grouping

and
Y¹, Y², Y³, Y⁴, Y⁵, Y⁶, Y⁷ and Y⁸ independently of one another each represent hydrogen, halogen, cyano, nitro; alkyl, alkoxy, alkylamino, dialkylamino, alkylthio, alkylsulphinyl or alkylsulphonyl having in each case 1 to 8 carbon atoms in the individual alkyl moieties;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms or
cycloalkyl having 3 to 6 carbon atoms,
R² represents hydroxyl, amino or represents alkyl, alkenyl, alkinyl, alkoxy, alkenyloxy, alkinyloxy, alkylamino, dialkylamino having in each case 1 to 4 carbon atoms in the respective alkyl moieties and being in each case optionally substituted by halogen, cyano or $C_1$–$C_4$-alkoxy, represents cycloalkyl, cycloalkenyl, cycloalkoxy, cycloalkenyloxy, cycloalkylamino, having 3 to 8 carbon atoms in the respective rings and being in each case in each case optionally substituted by halogen, cyano or $C_1$–$C_4$-alkoxy, or represents in each case optionally substituted phenyl, benzyl, benzyloxy, naphthyl, phenylamino or heterocyclyl having 3 to 8 ring members, the possible substituents preferably being selected from the list below:
halogen, cyano, nitro, amino, hydroxyl, formyl, carboxyl, carbamoyl, thiocarbamoyl;
alkyl, alkoxy, alkylthio, alkylsulphinyl or alkylsulphonyl having in each case 1 to 6 carbon atoms and being in each case straight-chain or branched; alkenyl or alkenyloxy having in each case 2 to 6 carbon atoms and being in each case straight-chain or branched;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched; alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms, or
R² represents one of the groupings below:

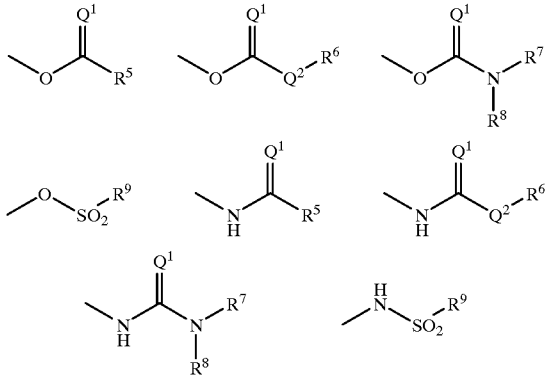

in which
Q¹ and Q² independently of one another each represent oxygen or sulphur,
R⁵ represents hydrogen or alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R⁶ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R⁷ represents hydrogen, alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
R⁸ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, or
R⁷ and R⁸ together with the linking nitrogen atom represent an optionally methyl-substituted heterocyclic ring,
R⁹ represents alkyl having 1 to 6 carbon atoms, dialkylamino having 1 to 4 carbon atoms in the individual alkyl moieties, heterocyclyl having 3 to 7 ring members which is attached via nitrogen or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, $R^3$ represents hydrogen or alkyl having 1 to 4 carbon atoms, pr $R^4$ represents aryl, cycloalkyl or cycloalkenyl having 3 to 8 carbon atoms , or heterocyclyl having 3 to 12 ring members, each of which is optionally mono- or polysubstituted by identical or different substituents, the possible substituents preferably being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

Cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms and straight-chain or branched halogenoalkyl having 1 to 4 carbon atoms and 1 to 9 identical or different halogen atoms and straight-chain or branched alkoxy or alkylthio having 1 to 4 carbon atoms and straight-chain or branched halogenoalkoxy or halogenoalkylthio having 1 to 4 carbon atoms and 1 to 9 identical or different halogen atoms and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

The invention relates in particular to compounds of the formula (IV-I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents selected from the group consisting of fluorine, chlorine, cyano and methoxy, Q represents oxygen or sulphur, $R^1$ represents a tricycle

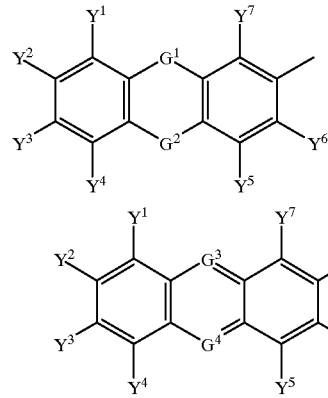

in which $G^1$ and $G^2$ independently of one another each represent a single bond, alkanediyl, alkenediyl, oxygen, sulphur, —NH—, -N(allyl)- or carbonyl and $G^3$ and $G^4$ independently of one another each represent nitrogen or a grouping

and $Y^1$, $Y^2$, $Y^3$, $Y^4$, $Y^5$, $Y^6$, $Y^7$ and $Y^8$ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents hydroxyl, amino or represents methyl, ethyl, n- or i-propyl, n-, i-, s- or t-butyl vinyl, allyl, propargyl, methoxy, ethoxy, allyloxy, propargyloxy, methylamino, ethylamino, dimethylamino, each of which is optionally substituted by halogen, cyano, methoxy or ethoxy, represents cyclopropyl, cyclobutyl, cyclopentyl, cyclohexyl, cyclopentyloxy, cyclohexyloxy, cyclopentylamino, cyclohexylamino, each of which is optionally substituted by halogen, cyano, methoxy or ethoxy, or represents phenyl, benzyl, benzyloxy, naphthyl, phenylamino or heterocyclyl having 3 to 8 ring members and being in each case optionally substituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoro- methylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl, or $R^2$ represents one of the groupings below:

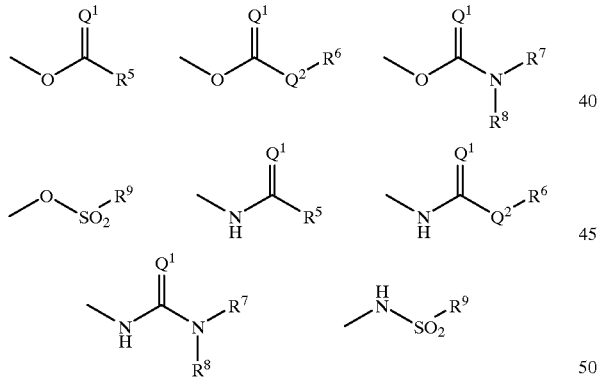

in which $Q^1$ and $Q^2$ independently of one another each represent oxygen or sulphur, $R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

Particular preference is given to compounds of the formula (IV-I) in which

A represents a single bond or represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1I-, 1,2- or 1,3-(2-methyl-propylene), optionally mono- or polysubstituted by identical or different substituents selected from the group consisting of fluorine, chlorine, cyano, methoxy, Q represents oxygen or sulphur,
R¹ represents a tricycle
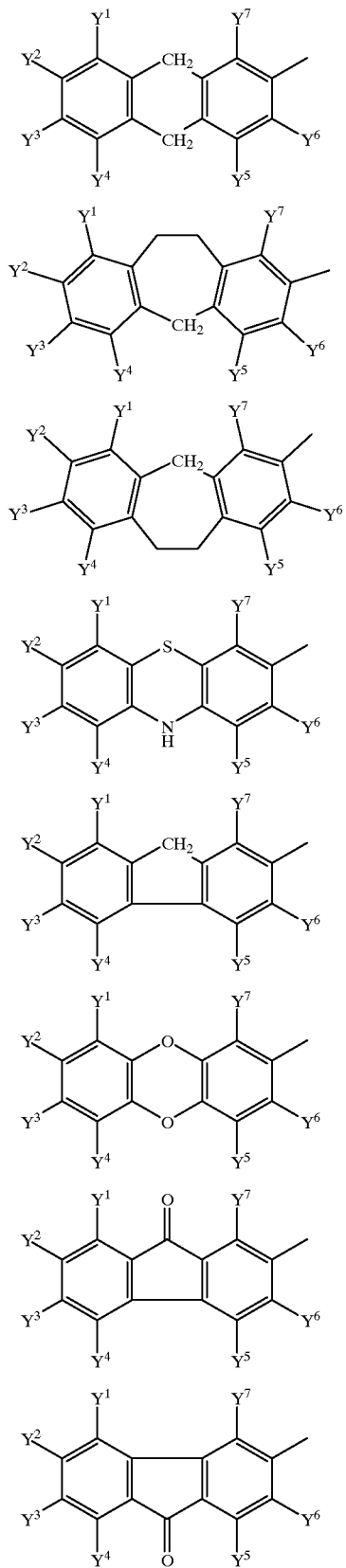
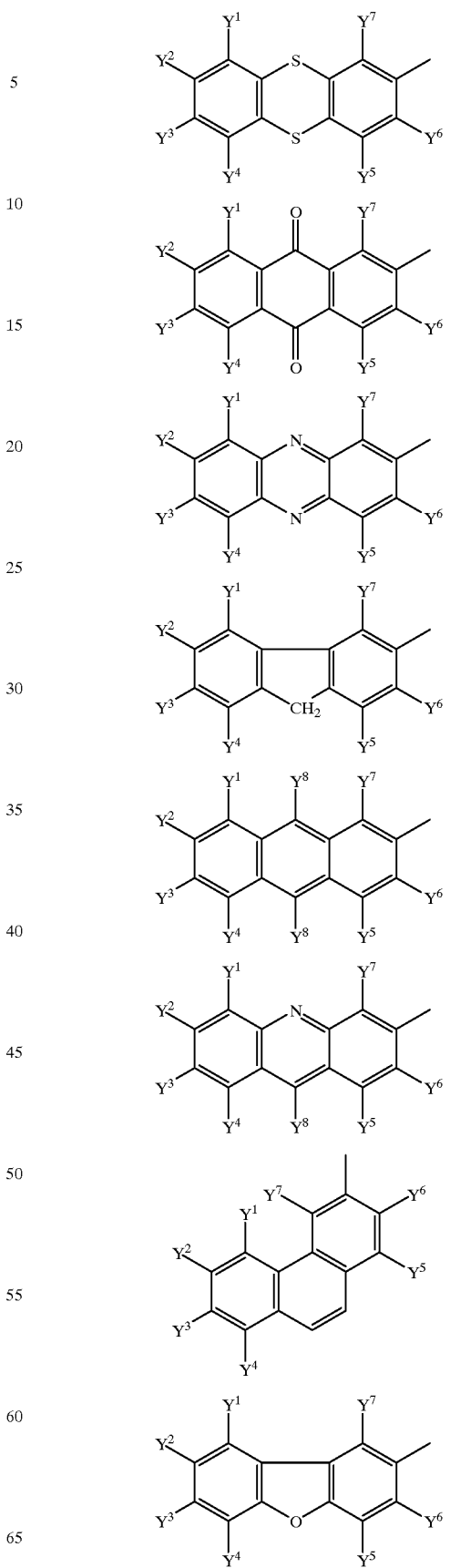

-continued

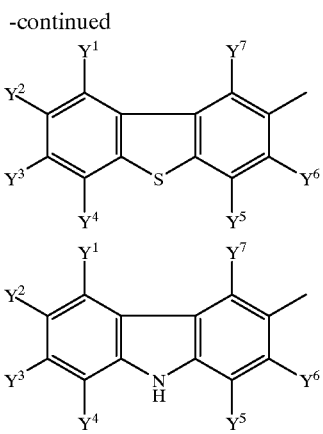

in which
Y¹, Y², Y³, Y⁴, Y⁵, Y⁶, Y⁷ and Y⁸ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or -trifluoromethylsulphonyl, methylamino, ethylamino, n- or i-propylamino, dimethylamino, diethylamino, cyclopropyl, cyclobutyl, cyclopentyl or cyclohexyl, R² represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, difluorochloromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the possible substituents preferably being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, represents-trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl, or R² represents one of the groupings below:

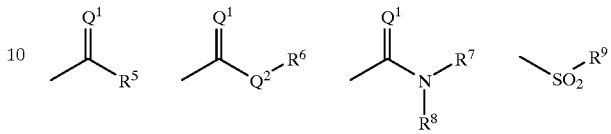

in which
Q¹ and Q² independently of one another each represent oxygen or sulphur, R⁵ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁶ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁷ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R⁸ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or R⁷ and R⁸ together with the linking nitrogen atom represent an optionally methyl-substituted heterocyclic ring, R⁹ represents methyl, ethyl, n- or i-propyl, n-, i-, s- or t-butyl, dimethylamino, diethylamino, pyrrolidin-1-yl, morpholin-N-yl, piperidin-1-yl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, R³ represents hydrogen or represents methyl,
R⁴ represents cyclopropyl, cyclobutyl, cyclopentyl or cyclohexyl, each of which is optionally mono- to hexasubstituted, preferred substituents being those mentioned below;
represents phenyl, naphthyl, furyl, benzofuranyl, pyrrolyl, indolyl, thienyl, benzothienyl oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the possible substituents preferably being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, represents trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, cyclopropyl, cyclobutyl, cyclopentyl or cyclohexyl.

A very particularly preferred group of compounds according to the invention are those compounds of the formula (IV-I) in which A represents a single bond or represents methylene, 1,1-ethylene, 1,2-ethylene, 1,1 -propylene, 1,2-propylene, 1,3-propylene or 2,2-propylene, Q represents oxygen, $R^1$ represents a tricycle

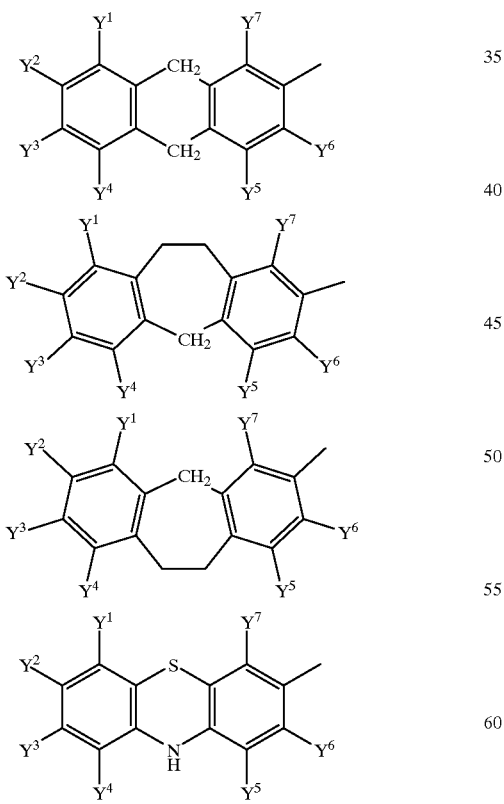

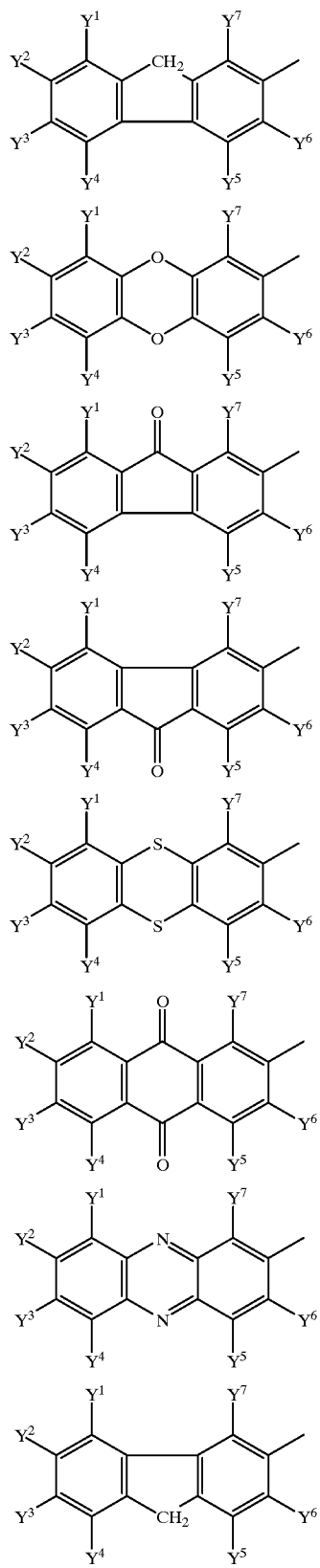

-continued

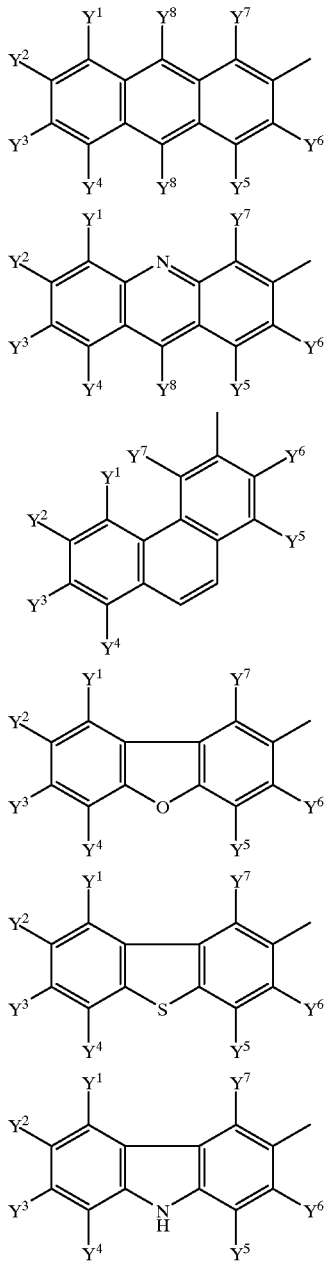

in which
Y¹, Y², Y³, Y⁴, Y⁵, Y⁶, Y⁷ and Y⁸ independently of one another each represent hydrogen, fluorine, chlorine, bromine, cyano, nitro, methyl, ethyl, n- or i-propyl, n-, i-, s- or t-butyl, n-pentyl, n-hexyl, n-heptyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, cyclopropyl, cyclobutyl, cyclopentyl or cyclohexyl, $R^2$ represents one of the groupings below:

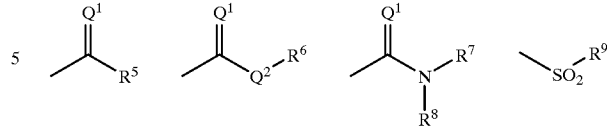

in which
$Q^1$ and $Q^2$ each represent oxygen,
$R^5$ represents hydrogen or methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or
$R^7$ and $R^8$ together with the linking nitrogen atom represent an optionally methyl-substituted heterocyclic ring,
$R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy,
$R^3$ represents hydrogen or methyl,
$R^4$ represents cyclohexyl or optionally mono- to trisubstituted phenyl, thienyl, furyl, benzofuryl, benzothienyl, pyridyl, pyrimidinyl, naphthyl, quinolyl, the possible substituents preferably being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

Particular preference is also given to compounds of the formula (IV-I) in which $R^2$ represents methoxy, fluoromethoxy, ethoxy, methylamino or dimethylamino.

Particular preference is also given to compounds of the formula (IV-I) in which $R^3$ represents hydrogen.

Particular preference is also given to compounds of the formula (IV-I) in which $R^4$ represents phenyl which is substituted by methoxy in position 3 and 4.

In a further particularly preferred group of compounds A represents —CH$_2$—CH$_2$—.

The radical definitions given above as general or as being preferred apply both to the end products of the formula (IV-I) and, correspondingly, to the starting materials and intermediates required in each case for the preparation.

These radical definitions can be combined with one another at will, i.e. including combinations between the given ranges of preferred compounds.

Furthermore, it has been found that the novel aryl glyoxylic acid amides of the general formula (IV-I) are obtained when Process IV-a) carboxylic acid derivatives of the general formula (IV-II)

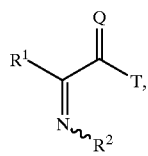

(IV-II)

in which
$R^1$, $R^2$ and Q are each as defined above and
T represents hydroxyl, halogen or alkoxy
are reacted with an amine of the general formula (IV-III)

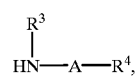

(IV-III)

in which
$R^3$, $R^4$ and A are each as defined above
or with a hydrohalide thereof,
if appropriate in the presence of an acid acceptor, if appropriate in the presence of a 9 condensing agent and if appropriate in the presence of a diluent, or when Process IV-b) glyoxylic acid amides of the general formula (IV-IV)

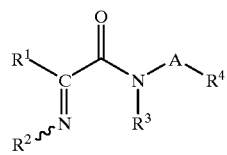

(IV-IV)

in which
A, $R^1$, $R^2$, $R^3$ and $R^4$ are each as defined above
are reacted with a sulphurizig agent, if appropriate in the presence of a diluent, or when Process IV-c) glyoxylic acid derivatives of the formula (IV-V)

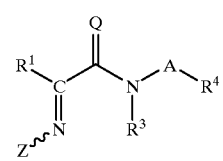

(IV-V)

in which
A, $R^1$, $R^3$ and $R^4$ are each as defined above and
Z represents hydroxyl or amino,
are reacted with an activated acid derivative of one of the formulae (VI) to (XIII),

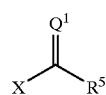

(IV-VI)

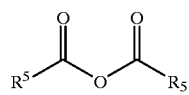

(IV-VII)

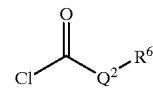

(IV-VIII)

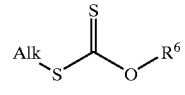

(IV-IX)

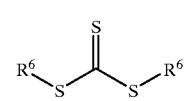

(IV-X)

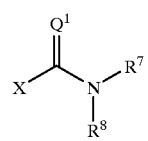

(IV-XI)

$R^7$—N=C=O (IV-XII)

$R^9$—SO$_2$Cl (IV-XIII)

in which
$R^5$, $R^6$, $R^7$, $R^8$ and $R^9$ are each as defined above, if appropriate in the presence of a diluent and if appropriate in the presence of a base.

The formula (IV-II) provides a general definition of the carboxylic acid derivatives required as starting materials for carrying out the process IV-a) according to the invention. In this formula (IV-I), Q and $R^1$ each preferably and in particular have those meanings which have already been mentioned in connection with the description of the compounds of the formula (IV-I) according to the invention as being preferred and as being particularly preferred, respectively, for Q and $R^1$; T preferably represents alkoxy having 1 to 4 carbon atoms, in particular methoxy or ethoxy, represents hydroxyl or chlorine.

The starting materials of the formula (IV-II) are known and/or can be prepared by processes which are known per se (cf. EP-A 178 826, EP-A 242 081, EP-A 382 375, EP-A 493 711, EP-A 432 503, DE-A 3 938 054, J. Heterocycl. Chem. (1990), 27(3), 487–95, Farmaco, Ed. Sci. (1980), 35(5), 394–404, Justus Liebigs Ann. Chem. (1969), 722, 38–44, Justus Liebigs Ann. Chem. (1969), 722, 29–37, Tetrahedron 1971, 3431–6).

The formula (IV-III) provides a general definition of the amines furthermore required as starting materials for carrying out the process IV-a) according to the invention. In this formula (IV-III), $R^3$, $R^4$ and A each preferably and in particular have those meanings which have already been mentioned in connection with the description of the compounds of the formula (IV-I) according to the invention as being preferred and as being particularly preferred, respectively, for $R^3$, $R^4$ and A.

The amines of the formula (IV-III) are known organic chemicals for synthesis and/or can be prepared by processes which are known per se.

The formula (IV-IV) provides a general definition of the glyoxylic acid amides required as starting materials for carrying out the process IV-b) according to the invention. In this formula (IV-IV), A, $R^1$, $R^2$, $R^3$ and $R^4$ each preferably and in particular have those meanings which have already been mentioned in connection with the description of the compounds of the formula (IV-I) according to the invention as being preferred and as being particularly preferred, respectively, for A, $R^1$, $R^2$, $R^3$ and $R^4$.

The glyoxylic acid amides of the general formula (IV-IV) are compounds according to the invention and can be obtained by the processes IV-a) or IV-c) according to the invention.

Suitable sulphurizing agents for carrying out the process IV-b) according to the invention are all reagents which are capable of exchanging oxygen atoms which are attached to carbon for sulphur atoms, such as, for example, hydrogen sulphide, phosphorus pentasulphide or Lawesson's Reagent The formula (IV-V) provides a general definition of the glyoxylic acid derivatives required as starting materials for carrying out the process IV-c) according to the invention. In this formula (IV-V), A, $R^1$, $R^3$ and $R^4$ each preferably in particular have those meanings which have already been mentioned in connection with the description of the compounds of the formula (IV-I) according to the invention as being preferred and as being particularly preferred, respectively, for A, $R^1$, $R^3$ and $R^4$. Z represents hydroxyl or amino.

The starting materials of formula (IV-V) are compounds according to the invention and can be obtained by the processes IV-a) or IV-b) according to the invention.

The formulae (IV-VI) to (IV-XI) provide general definitions of the activated acid derivatives furthermore required for carrying out the process IV-c) according to the invention for preparing the compounds of the formula (IV-I) according to the invention. In these formulae (IV-VI) to (IV-XIII), $R^5$, $R^6$, $R^7$, $R^8$ and $R^9$ each preferably and in particular have those meanings which have already been mentioned in connection with the description of the compounds of the formula (IV-I) according to the invention as being preferred and as being particularly preferred, respectively, for $R^5$, $R^6$, $R^7$, $R^8$ and $R^9$.

The activated acid derivatives of the formulae (IV-VI) to (IV-XI) are known organic chemicals for synthesis and/or can be prepared by processes which are known per se.

The process IV-a) according to the invention is, if appropriate, carried out in the presence of a diluent. Suitable diluents for carrying out the process according to the invention are water and organic solvents. These include in particular aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether, ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, sulphoxides, such as dimethyl sulphoxide, alcohols, such as methanol, ethanol, n- or i-propanol, ethylene glycol, ethylene glycol monomethyl ether, ethylene glycol monoethyl ether, diethylene glycol monomethyl ether, diethylene glycol monoethyl ether, mixtures thereof with water or pure water.

The process IV-a) according to the invention is, if appropriate, carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N,N-dimethylaminopyridine, diazabicyclooctane (DABCO), diazabicyclononene (DBN) or diazabicycloundecene (DBU).

The process IV-a) according to the invention is, if appropriate, carried out in the presence of a suitable condensing agent. Suitable condensing agents are all condensing agents which are customarily used for such amidation reactions. Examples which may be mentioned are acyl halide formers such as phosgene, phosphorus tribromide, phosphorous trichloride, phosphorus pentachloride, phosphorus oxychloride or thionyl chloride; anhydride formers such as ethyl chloroformate, methyl chloroformate or methanesulphonyl chloride; carbodiimides, such as N,N'-dicyclohexylcarbodiimide (DCC) or other customary condensing agents, such as phosphorus pentoxide, polyphosphoric acid, N,N'-carbonyldiimidazole, 2-ethoxy-N-ethoxycarbonyl-1,2-dihydroquinoline (EEDQ) or triphenyl phosphine/carbon tetrachloride.

The process IV-a) according to the invention is, if appropriate, carried out in the presence of a catalyst.

Examples which may be mentioned are 4-dimethylaminopyridine, 1-hydroxy-benzotriazole or dimethylformamide.

When carrying out the process IV-a) according to the invention, the reaction temperatures can be varied within a relatively wide range. In general, the reaction is carried out at temperatures between −20° C. and +200° C., preferably at temperatures between 0° C. and 150° C.

For carrying out the process IV-a) according to the invention, generally 1 to 5 mol, preferably 1.0 to 2.5 mol, of amine are employed per mole of carboxylic acid derivative of the formula (IV-II).

The practice of the reaction and the work-up and the isolation of the reaction products are carried by known processes (cf. the Preparation Examples).

The process IV-a) according to the invention can also be carried out as a two-step process. The carboxylic acid derivatives of the general formula (IV-II) are then initially converted into an activated form and, in a subsequent step, reacted with the amines of the general formula (IV-III) to give the alkoximinoacetic acid derivatives of the general formula (IV-I) according to the invention.

Suitable activated forms of the carboxylic acid derivatives of the formula (IV-II) are all carboxy-activated derivatives, such as, for example, acyl halides, preferably acyl chlorides, acid azides, furthermore symmetric and mixed anhydrides, such as, for example, the mixed 0-alkylcarbonic anhydrides, furthermore activated esters, such as, for example, p-nitrophenyl esters or N-hydroxysuccinimide esters and also adducts with condensing agents, such as, for example, dicyclohexylcarbodiimide or in situ generated activated forms of the carboxylic acids.

Suitable diluents for carrying out the process IVb) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2- dimethoxyethane, 1,2-diethoxyethane or anisole.

When carrying out the process IV-b) according to the invention, the reaction temperatures can be varied within a relatively wide range. In general, the reaction is carried out at temperatures of from 0° C. to 1 50° C., preferably at temperatures of from 0° C. to 80° C.

For carrying out the process IV-b) according to the invention for preparing the compounds of the formula (IV-I) according to the invention, generally 0.1 to 15 mol, preferably 0.5 to 8 mol of sulphurizing agent are employed per mole of the glyoxylic acid amide of the formula (I-IV).

Suitable diluents for carrying out the process IV-c) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2- dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate; sulphoxides, such as dimethyl sulphoxide; or sulphones, such as sulpholane.

The process IV-c) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process IV-c) according to the invention, the reaction temperatures can be varied within a relatively wide range. In general, the reaction is carried out at temperatures of from 0° C. to 150° C., preferably at temperatures of from 0° C. to 80° C.

For carrying out the process IV-c) according to the invention for preparing the compounds of the formula (IV-I), generally 1 to 15 mol, preferably 2 to 8 mol, of activated acid derivative of one of the formulae (IV-VI) to (IV-XI) are employed per mole of the glyoxylic acid derivative of the formula (IV-V).

The processes according to the invention are generally carried out under atmospheric pressure. However, it is also possible to operate under elevated or reduced pressure—in general between 0.1 bar and 10 bar.

The practice of the reaction and the work-up and the isolation of the reaction products are carried out by known processes (cf. the Preparation Examples).

The active compounds according to the invention have a potent microbicidal activity and can be employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*
Plasmopara species, such as, for example, *Plasmopara viticola;*
Bremia species, such as, for example, *Bremia lactucae,*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Sclerotinia species, such as, for example, *Sclerotinia sclerotiorum;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;* and
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling diseases in viticulture and fruit and egtable growing, such as, for example, against Plasmopara and Phytophthora species.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90° C.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofaam, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropinorph, fentin acetate, fentin hydroxide, ferbam, fermizone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfiur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G, OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-hydroxy-2,2,7,7-tetramethyl-5-1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)ethyl] amino]carbonyl]propyl}-carbamate, 1-(2,4-dichlorophenyl)2-(1H-1,2,4-triazol-1-yl)ethanone-O-(phenylmethyl)-oxime, 1-(2-methyl-1-naphthalenyl)1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4chlorophenyl)-3-phenyloxiranyl]-methyl]-1H-1,2,4triazole, 1-[1-[2-[(2,4-dichlorophenyl)methoxy]phenyl]ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)ethyl]-1-ethyl-3-methyl-cyclopropanecarboxamide, 2,6-dichloro-5-methylthio)4-pyrimidinyl-thiocyanate, 2,6-dichloro-N-(4-trifluoromethylbenzyl)-benzamide, 2,6-dichloro-N-[[4-(trifluoromethyl)phenyl]methyl]-benzamide, 2-(2,3,3-triiodo-2-propenyl)2H-tetrazole, 2-[(1-methylethyl)sulphonyl]-5-trichloromethyl-1,3,4-thiadiazole, 2-[[6deoxy-4-O-(4-O-methyl-β-D-glycopyranosyl)-α-D-glucopyranosyl]-amino]-4-methoxy-1H-pyrrolo[2,3d]pyrimidine-5-carbonitrile, 2-aminobutane, 2-bromo-2-(bromomethyl)-pentanedinitrile, 2-chloro-N-2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano-[(1-methyl-2-propynyl)oxy]methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-4-methylphenyl)-1H-imidazole-1-sulphonamide, 4-methyl-tetrazolo[1,5-a]quinazolin-5(4H)-one, 8-(1,1-dimethylethyl)N-ethyl-N-propyl-1,4-dioxaspiro[4.5] decane-2-methanamine, 8-hydroxyquinoline sulphate, 9H-xanthene-2-[(phenylamino)-carbonyl]-9-carboxylic hydrazide, bis-(1-methylethyl-3-methyl-4-[(3-methylbenzoyl)oxy]-2,5-thiophenedicarboxylate, cis-1-chlorophenyl)2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, ethyl [(4-chlorophenyl)-azo]-cyanoacetate, potassium bicarbonate, methanetetrathiol, -sodium salt, methyl 1-(2,3-dihydro-2,2dimethyl-1H-inden-1-yl)-1H-imidazole-5-carboxylate, methyl N-2,6-dimethylphenyl)-N-(5-isoxazolylcarbonyl)-DL-alaninate, methyl N-(chloroacetyl)-N-(2,6-dimethylphenyl)DL-alaninate, N-(2,3-dichloro-4-hydroxyphenyl)-1-methyl-cyclohexanecarboxamide, N-(2,6-dimethylphenyl)-2-methoxy-N-tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)4-methyl-3-nitro-benzenesulphonamide, N-(4-cyclohexylphenyl)-1,4,5,6-tetrahydro-2-pyrimidinamine, N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine,-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides:
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-4-chlorophenyl)-1-ethoxymethyl)-5-trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxin, butylpyridaben,
cadusafos, carbaryl, carbofuran, carbophenothiop, caibosulfan, cartap, chloethocarb, chlorethoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocyirin, clofentezine, cyanophos, cycloprothrin, cyfluthrin, cyhalotirin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin, lambda-cyhalotmrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenophos, promecarb, propaphos, propoxur, prothiophos, prothoate, pymetrozin, pyrachlophos, pyridaphenthion, pyresmelirin, pyretrum, pyridaben, pyrimidifen, pyriproxifen, quinalphos,
salithion, sebufos, silafluofen, sulfotep, sulprofos,
tebufenozide, tebufenpyrad, tebupirimphos, teflubenzuron, tefluthrin, temephos, terbam, terbufos, tetrachlorvinphos,
thiafenox, thiodicarb, thiofanox, thiomethon, thionazin, thuringiensin, tralometluin, triarathen, triazophos, triazuron, trichlorfon, triflumuron, trinethacarb,
vamidothion, XMC, xylylcarb, zetamethrin.

It is also possible to admix other known active compounds, such as herbicides, fertilizers and growth regulators.

The active compounds according to the invention can be used as such or in the form of their commercial formulations or the use forms prepared therefrom, such as ready-to-use solutions, suspensions, wettable powders, pastes, soluble powders, dusts and granules. They are used in the customary manner, for example by pouring, spraying, atomizing, broadcasting, foaming, brushing-on and the like. It is further possible to apply the active compounds by the ultra-low volume method or to inject the preparation of active compound, or the active compound itself, into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

The active compounds are suitable for controlling animal pests, in particular insects, arachnids and nematodes, which are encountered in agriculture, in forestry, in the protection of stored products and of materials, and in the hygiene field, and have good plant tolerance and favourable toxicity to warm-blooded animals. They may be preferably employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphigus spp., *Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., Trichoplusia ni, *Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fiiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erydtrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Omithodoros spp., *Dermanyssus gallinae, Eriophyes ribis, Phyllocoptuta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp. and Trichodorus spp.

The compounds of the formula (II-I) according to the invention can be employed particularly successfully for controlling plant-damaging insects, such as, for example, against the larvae of the beet-army worm (*Spodoptera frugiperda*).

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

In the case of the use of water as an extender, organic solvents can, for example, also be used as auxiliary solvents. Essentially, the following are suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and factionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself The active compound content of the us e forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, Haematopinus spp., Linognathus spp., Pediculus spp., Phtirus spp. and Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp. and Felicola spp.

From the order of the Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example *Blatta orientalis, Periplaneta americana, Blattela germanica* and Supella spp.

From the subclass of the Acaria (Acarida) and the orders of the Meta- and Mesostigmata, for example, Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Stemostoma spp. and Varroa spp.

From the order of the Actinedida (Prostigmata) und Acaridida (Astigmata), for example, Acarapis spp., Cheyletiella spp., Onithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds of the formula (II-I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of molded articles containing the active compound, such as collars, ear marks, tail marks, limb bands, halters, marking devices and the like.

When used for cattle, poultry, pets and the like, the active compounds of the formula (II-I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds of the formula (II-I) according to the invention also have a potential insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec. Tryptodendron spec. Apate monachus, *Bostrychus capucins, Heterobostrychus brunneus,* Sinoxylon spec. *Dinoderus minutus*

Hymenopterons, such as

*Sirex juvencus, Urocerus gigas, Urocerus gigas taignus, Urocerus augur*

Termites, such as

*Kalotermes flavicollis, Cryptotermes brevis, Heterotennes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and wood processed wood products which can be protected by the agents according to the invention or mixtures comprising these are to be understood as meaning, for example: building timber, wooden beams, railway sleepers, bridge components, boat jetties, wooden vehicles, boxes, pallets, containers, telegraph poles, wood paneling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture or an aliphatic polar organic chemical solvent or solvent mixture is replaced. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and also fingicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The preparation and the use of the active compounds according to the invention is illustrated by the examples below.

PREPARATION EXAMPLES

Example I-1

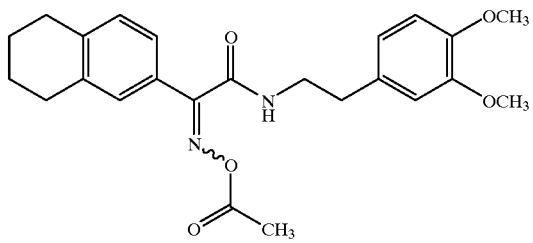

1.91 g (5 mmol) of N-[(3,4ethoxyphenyl)-2-ethyl]-2-hydroxyimio-2-2-tetrahydronaphthyl)-acetamide are dissolved in 20 -ml of methylene chloride and, at −5° C., 0.785 g (10 mmol) of acetyl chloride, dissolved in 5 ml. of methylene chloride, are added dropwise. The mixture is stirred for another 10 minutes, a solution of 1.4 ml (10 mmol) of triethylamine and 5 ml of methylene chloride is then added dropwise and the mixture is stirred for a further 2 hours at 0° C. After the mixture has warmed to room temperature, it is washed repeatedly with water, the organic phase is dried over sodium sulphate and the solvent is distilled off under reduced pressure.

This gives 2.0 g (95% of theory) of N-[(3,4-dimethoxyphenyl)-2-ethyl]-2-acetoxyimino-2-(2-tetrahydronaphthyl)-acetamide as a colourless oil.

1H-NMR: δ (ppm)=2.13 (s, 3H).

Preparation of the Starting Material:

Example I-II-1

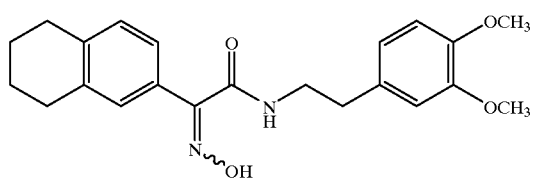

16.8 g (0.0679 mol) of ethyl 2-hydroximino-2-(2-tetrahydronaphthyl)-acetate, 12.3 g (0.0679 mol) of 2-(3,4-dimethoxyphenyl)-ethylamine and 24.4 g (0.136 mol) of a 30% strength sodium methoxide solution in 100 ml of methanol are heated at the boil and under reflux for 16 hours. The solvent is distilled off and the residue is then taken up in dichloromethane and washed repeatedly with water. The organic phase is dried over sodium sulphate and the solvent is distilled off under reduced pressure.

This gives 21.4 g (82.3% of theory) of N-[(3,4-dimethoxyphenyl)-2-ethyl]-2-hydroxyimino-2-(2-tetrahydronaphthyl)-acetamide as a solid of melting point 104° C.

Similarly to Example I-1, and in accordance with the general description of the preparation process according to the invention, it is also possible to prepare, for example, the compounds listed in Table I-8 below:

TABLE I-8

(I-I)

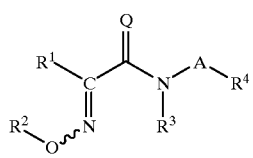

| Ex. No. | $R^1$ | $R^2$ | $R^3$ | A | $R^4$ | Phys. Data |
|---|---|---|---|---|---|---|
| I-2 | (tetrahydronaphthyl) | —COOCH$_3$ | H | —CH$_2$—CH$_2$— | 3,4-dimethoxyphenyl | $^1$H-NMR:*): 3.81 ppm(s, 3H) |
| I-3 | (tetrahydronaphthyl) | —COOC$_2$H$_5$ | H | —CH$_2$—CH$_2$— | 3,4-dimethoxyphenyl | logP: 3.19/3.55 |
| I-4 | (tetrahydronaphthyl) | —COO-iPr | H | —CH$_2$—CH$_2$— | 3,4-dimethoxyphenyl | logP: 3.55/3.84 |

TABLE I-8-continued

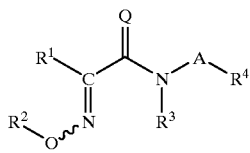

(I-I)

| Ex. No. | R¹ | R² | R³ | A | R⁴ | Phys. Data |
|---|---|---|---|---|---|---|
| I-5 | (6-methyl-tetrahydronaphthyl) | —COOPh | H | —CH₂—CH₂— | 3,4-dimethoxyphenyl | logP: 3.82/4.09 |
| I-6 | (6-methyl-tetrahydronaphthyl) | —COO-cyclohexyl ester group | H | —CH₂—CH₂— | 3,4-dimethoxyphenyl | logP: 4.20/4.62 |
| I-7 | (6-methyl-tetrahydronaphthyl) | —COPh | H | —CH₂—CH₂— | 3,4-dimethoxyphenyl | logP: 3.69/4.10 |
| I-8 | 4-bromophenyl | —COCH₃ | H | —CH₂—CH₂— | 3,4-dimethoxyphenyl | ¹H-NMR*): 3.87 ppm(s, 6H) |
| I-9 | 4-bromophenyl | —COOCH₃ | H | —CH₂—CH₂— | 3,4-dimethoxyphenyl | ¹H-NMR*): 3.88 ppm(s, 6H) |
| I-10 | 4-bromophenyl | —COOC₂H₅ | H | —CH₂—CH₂— | 3,4-dimethoxyphenyl | logP: 3.19 |
| I-11 | (5-methyl-indanyl) | —COOCH₃ | H | —CH₂—CH₂— | 3,4-dimethoxyphenyl | logP: 2.78/2.97 |
| I-12 | (5-methyl-indanyl) | —COCH₃ | H | —CH₂—CH₂— | 3,4-dimethoxyphenyl | logP: 2.65/2.87 |
| I-13 | (5-methyl-indanyl) | —COOC₂H₅ | H | —CH₂—CH₂— | 3,4-dimethoxyphenyl | logP: 3.04/3.27 |
| I-14 | 4-ethylphenyl | —COOCH₃ | H | —CH₂—CH₂— | 3,4-dimethoxyphenyl | logP: 2.73/2.94 |
| I-15 | 4-ethylphenyl | —COOC₂H₅ | H | —CH₂—CH₂— | 3,4-dimethoxyphenyl | logP: 2.98 |
| I-16 | 4-ethylphenyl | —COCH₃ | H | —CH₂—CH₂— | 3,4-dimethoxyphenyl | logP: 2.42/2.60 |
| I-17 | 4-Chlorphenyl | —COCH₃ | H | —CH₂—CH₂— | 3,4-dimethoxyphenyl | ¹H-NMR*): 3.87 ppm (s, 6H) |

*)The $^1$H-NMR spectra were recorded in deuterochloroform (CDCl$_3$) or hexa-deuterodimethyl sulphoxide (DMSO-d$_6$) using tetramethylsilane (TMS) as internal standard. The chemical shift is given as δ value in ppm.

USE EXAMPLES

Example I-A

Phytophthora-Test (Tomato)/protective
Solvent: 47 parts by weight of acetone
Emulsifier: 3 parts by weight of alkylaxyl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of the active compound until dew-moist. After the spray coating has dried on, the plants are inoculated with an aqueous spore suspension of Phytophthora infestans.

The plants are placed in an incubation cabin at approximately 20° C. and 100% relative atmospheric humidity.

Evaluation is carried out 3 days after the inoculation. An efficacy of 0% means that the disease level on the treated plants corresponds to that of the untreated control, while an efficacy of 100% means that no disease is observed on the treated plants.

In this test, for example the following compound (I-1) of the Preparation Examples exhibits, at an exemplary active compound application rate of 50 g/ha, an efficacy of 95% compared to the untreated control.

Example I-B
Tetranychus-Test (OP-resistant/dip treatment)
Solvent:
   7.5 parts by weight of dimethylformamide
   100 parts by weight of methanol
Emulsifier: 2.5 parts by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested by all stages of the greenhouse red spider mite (*Tetranychus urticae*) are treated by being dipped into a preparation of the active compound of the desired concentration.

After the desired period of time, the activity in % is determined. 100% means that all spider mites have been killed; 0% means that none of the spider mites have been killed.

In this test, for example the compound (I-14) of the Preparation Examples effects, at an exemplary active compound concentration of 0.05%, a kill of 100% after 7 days.

PREPARATION EXAMPLES

Example II-1

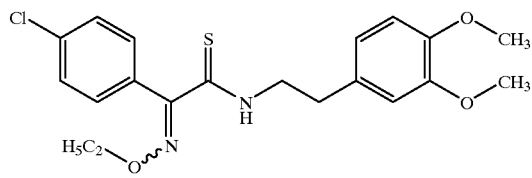

2.0 g (5 mmol) of 2,4-bis-(4-methoxyphenyl)-1,3-dithia-2,4-diphosphetan 2,4-disulphide (Lawesson's Reagent) are added to a solution of 3.9 g (10 mmol) of N-[2-(3,4-dimethoxyphenyl)-ethyl]-2-ethoximino-2-(4-chlorophenyl)-acetamide in 60 ml of tetrahydrofuran. The mixture is heated at the boil and under reflux for 6 hours. The solvent is distilled off under reduced pressure and the residue is chromatographed over silica gel using petroleum ether/ethyl acetate (2:1).

This gives 1.9 g (47% of theory) of N-[2-(3,4-dimethoxyphenyl)-ethyl]-2-ethoximino-2-(4-chlorophenyl)-thioacetamide as e/z isomer mixture.

HPLC: logP=3.73 (e-isomer), 4.03 (z-isomer)

Preparation of the Starting Material:

Example II-II-1

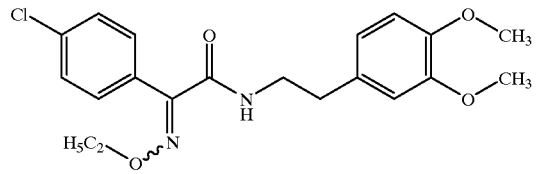

2.55 g (10 mmol) of ethyl $^2$-ethoximino-2-(4-chloro)phenylacetate are initially charged in 50 ml of methanol and 1.81 g (10 mmol) of 2-(3,4-dimethoxyphenyl)ethylamine and 3.6 g (20 mmol) of 30% strength methanolic sodium methoxide solution are then added successively at room temperature. The mixture is stirred at 65° C. for 20 hours and the solvent is then distilled off, and the residue is taken up in methylene chloride, washed successively with water, dilute hydrochloric acid and water and dried over sodium sulphate. The solvent is distilled off and the residue is chromatographed over silica gel using petroleum ether/ethyl acetate (1:1).

This gives 1.2 g (31% of theory) of N-[2-3,4dimethoxyphenyl)-ethyl]-2-ethoximino-2(-4-chlorophenyl)-acetamide as E/Z mixture.

E isomer: logP 3.07; Z isomer: logP 3.34.

Similarly to Example II-1, and in accordance with the general description of the preparation process according to the invention, it is also possible to prepare, for example, the compounds listed in Table II-8 below:

TABLE II-8

(II-Ie)

$$\text{structure}$$

| Ex. No. | R$^1$ | R$^2$ | A | R$^4$ | Phys. Data*) |
|---|---|---|---|---|---|
| II-2 | 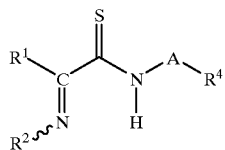 | —O—C$_2$H$_5$ | —CH$_2$—CH$_2$— | 3,4-dimethoxyphenyl | logP: 4.13/4.41 |
| II-3 | 4-methylphenyl | —O—CH$_3$ | —CH$_2$—CH$_2$— | 3,4-dimethoxyphenyl | logP: 3.15/3.41 |
| II-4 | 4-ethylphenyl | —O—CH$_3$ | —CH$_2$—CH$_2$— | 3,4-dimethoxyphenyl | logP: 3.50/3.77 |
| II-5 | 4-bromophenyl | —O—C$_2$H$_5$ | —CH$_2$—CH$_2$— | 3,4-dimethoxyphenyl | logP: 3.82/4.14 |
| II-6 | 4-bromophenyl | —O—CH$_3$ | —CH$_2$—CH$_2$— | 3,4-dimethoxyphenyl | logP: 3.50/3.80 |

TABLE II-8-continued (II-Ie)

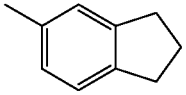

| Ex. No. | R¹ | R² | A | R⁴ | Phys. Data*) |
|---|---|---|---|---|---|
| II-7 | 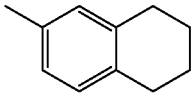 | —O—CH₃ | —CH₂—CH₂— | 3,4-dimethoxyphenyl | m.p.: 83–84° C. |
| II-8 | 3-ethylphenyl | —O—C₂H₅ | —CH₂—CH₂— | 3,4-dimethoxyphenyl | logP: 3.82/4.09 |
| II-9 | 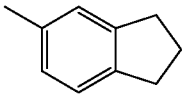 | —O—CH₃ | —CH₂—CH₂— | 3,4-dimethoxyphenyl | m.p.: 132–133° C. |
| II-10 | 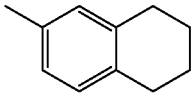 | —O—C₂H₅ | —CH₂—CH₂— | 3,4-dimethoxyphenyl | logP: 3.87/4.13 |

*)The $^1$H-NMR spectra were recorded in deuterochloroform (CDCl₃) or hexa-deuterodimethyl sulphoxide (DMSO-d₆) using tetramethylsilane (TMS) as internal standard. The chemical shift is given as δ value in ppm.

USE EXAMPLES

Example II-A

Phytophthora-Test (Tomato)/protective
Solvent: 47 parts by weight of acetone
Emulsifier: 3 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of the active compound until dew-moist. After the spray coating has dried on, the plants are inoculated with an aqueous spore suspension of Phytophthora infestans.

The plants are placed in an incubation cabin at approximately 20° C. and 100% relative atmospheric humidity.

Evaluation is carried out 3 days after the inoculation. An efficacy of 0% means that the disease level on the treated plants corresponds to that of the untreated control, while an efficacy of 100% means that no disease is observed on the treated plants.

In this test, for example the following compounds (II-2), (II-6) and (II-7) of the Preparation Examples exhibit, at an exemplary active compound application rate of 50 g/ha, an efficacy of 80 to 94% compared to the untreated control.

Example II-B

Plasmopara-Test (Grapevines)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of the active compound until dew-moist. After the spray coating has dried on, the plants are inoculated with an aqueous spore suspension of Plasmopara viticola and then remain in an incubation cabin at 20° C. and 100% relative atmospheric humidity for 1 day. The plants are subsequently placed in a greenhouse at 21° C. and approximately 90% atmospheric humidity for 5 days. The plants are then moistened and placed in an incubation cabin for 1 day.

Evaluation is carried out 6 days after the inoculation. An efficacy of 0% means that the disease level on the treated plants corresponds to that of the untreated control, while an efficacy of 100% means that no disease is observed on the treated plants.

In this test, for example the following compound (II-6) of the Preparation Examples exhibits, at an exemplary active compound application rate of 50 g/ha, an efficacy of 89% compared to the untreated control.

Example II-C

Spodoptera test
Solvent:
  100 parts by weight of acetone
  1900 parts by weight of methanol To prepare a suitable preparation of active compound, 1 part by weight of active compound is mixed with the stated amount of solvent and the stated amount of emulsifier and the concentrate is diluted with emulsifier-containing water to the desired concentration.

A stated amount of the preparation of active compound of the desired concentration is pipetted onto a standardized amount of synthetic feed. In 3 replications, one larva (L₂–L₃) each of the beet army-worm (Spodoptera frugiperda) is placed on the feed.

After the desired period of time, the kill in % is determined. 100% means that all animals have been killed; 0% means that none of the animals have been killed.

In this test, for example the following compound (II-4) of the Preparation Examples exhibits, at an exemplary active compound concentration of 0.05%, a kill of 100% after 9 days.

PREPARATION EXAMPLES

Example III-1

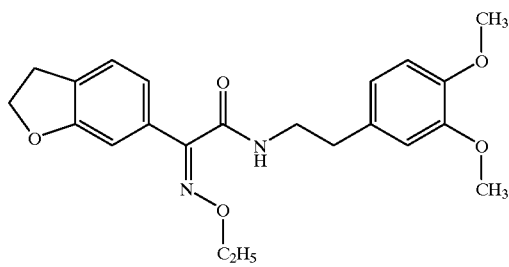

At 20° C., 1.81 g (10 mmol) of 2-(3,4-dimethoxyphenyl)-ethylamine and 3.6 g (20 mmol) of 30% strength methanolic sodium methoxide solution are added successively to a solution of 2.63 g (10 mmol) of ethyl 2-(2,3-dihydrobenzofuran-6-yl)-2-ethoximinoacetate in 50 ml of methanol. The mixture is stirred at 65° C. for 20 hours and the solvent is then distilled off. The residue is taken up in methylene chloride and washed first with water, then with dilute hydrochloric acid and once more with water and dried over sodium sulphate. The solvent is distilled off and the residue is then chromatographed over silica gel using petroleum ether/ethyl acetate (1:1).

This gives 2.7 g (68% of theory) of N-[2-(3,4dimethoxyphenyl)-ethyl]-2-(2,3-dihydrobenzofuran-6-yl) 2-ethoximino-acetamide of melting point 78° C.

Similarly to Examples III-1, and in accordance with the general description of the preparation process according to the invention, it is also possible to prepare, for example, the compounds listed in Table III-1 below:

USE EXAMPLES

Example III-A

Phytophthora-Test (Tomato)/protective

Solvent: 47 parts by weight of acetone
Emulsifier: 3 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of the active compound until dew-moist After the spray coating has dried on, the plants are inoculated with an aqueous spore suspension of Phytophthora infestans.

The plants are placed in an incubation cabin at approximately 20° C. and 100% relative atmospheric humidity.

Evaluation is carried out 3 days after the inoculation. An efficacy of 0% means that the disease level on the treated plants corresponds to that of the untreated control, while an efficacy of 100% means that no disease is observed on the treated plants.

In this test, for example the compound (III-1) of the Preparation Examples exhibits, at an exemplary active compound application rate of 500 g/ha, an efficacy of 95% compared to the untreated control.

TABLE III-1

III-Ia

| Ex. No. | $R^1$ | $R^2$ | A | $R^4$ | Isomer | m.p. (° C.) |
|---|---|---|---|---|---|---|
| III-2 | 6-methyl-2,3-dihydrobenzofuranyl | —$CH_3$ | —$CH_2$—$CH_2$— | 3,4-dimethoxyphenyl | e/z mixture | logP: 2.24/2.46 |
| III-3 | 6-methyl-2,3-dihydrobenzofuranyl | —$C_2H_5$ | —$CH_2$—$CH_2$— | 3,4-dimethoxyphenyl | e | 83–84 |

PREPARATION EXAMPLES

Example IV-1

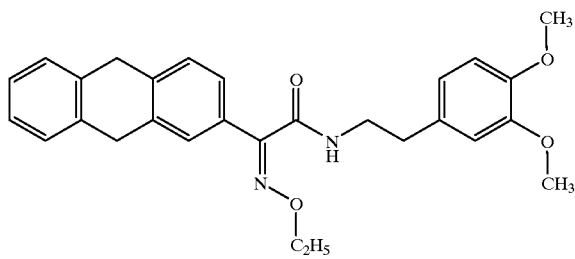

At 20° C., 1.81 g (10 mmol) of 2-(3,4-dimethoxyphenyl)-ethylamine and 3.6 g (20mmol) of 30% strength methanolic sodium methoxide solution are added successively to a solution of 3.22 g (10 mmol) of ethyl 2-(9,10-dihydroanthracen-2-yl)-2-ethoximinoacetate in 50 ml of methanol. The mixture is stirred at 20° C. for 20 hours and the solvent is then distilled off. The residue is taken up in methylene chloride and washed first with water, then with dilute hydrochloric acid and once more with water and dried over sodium sulphate. The solvent is distilled off and the residue is chromatographed over silica gel using petroleum ether/ethyl acetate (2:1).

This gives 1.3 g (28% of theory) of N-[2-(3, 4dimethoxyphenyl)-ethyl]-2-9,10-dihydroanthracen-2-yl)-2-ethoximino-acetamide as an oil and as a mixture of stereoisomers.

HPLC: logP:

3.62 (e isomer)

4.00 (z isomer)

Similarly to Examples IV-1, and according to the general description of the preparation process according to the invention, it is also possible to prepare, for example, the compounds listed in Table IV-1 below:

TABLE IV-1

IV-Ia

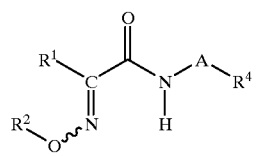

| Ex. No. | $R^1$ | $R^2$ | A | $R^4$ | Isomer | m.p. (° C.) |
|---|---|---|---|---|---|---|
| IV-2 | 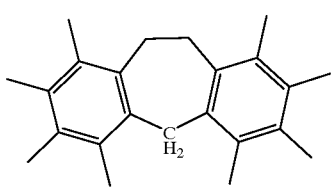 | —CH$_3$ | —CH$_2$—CH$_2$— | 3,4-dimethoxyphenyl | e/z mixture | logP: 3.61/3.87 |
| IV-3 | 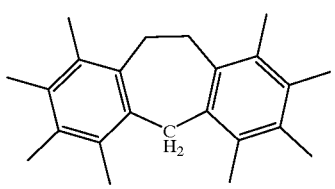 | —C$_2$H$_5$ | —CH$_2$—CH$_2$— | 3,4-dimethoxyphenyl | e/z mixture | logP: 3.91/4.20 |

TABLE IV-1-continued

IV-Ia

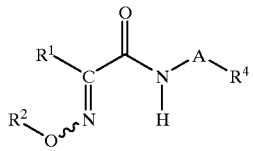

| Ex. No. | R¹ | R² | A | R⁴ | Isomer | m.p. (° C.) |
|---|---|---|---|---|---|---|
| IV-4 | 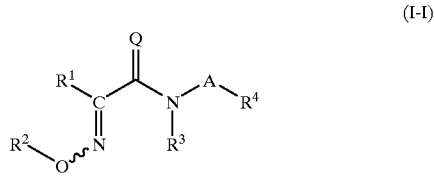 | —CH₃ | —CH₂—CH₂— | 3,4-dimethoxyphenyl | e/z mixture | logP: 3.31/3.68 |

USE EXAMPLES

Example IV-A

Phytophthora-Test (Tomato)/protective
Solvent: 47 parts by weight of acetone
Emulsifier: 3 parts by weight of alkylaryl polyglycol ether To prepare a suitable preparation of active compound, 1 part by weight of active compound is mixed with the stated amounts of solvent and emulsifier, and the concentrate is diluted with water to the desired concentration.

To test for protective activity, young plants are sprayed with the preparation of the active compound until dew-moist. After the spray coating has dried on, the plants are inoculated with an aqueous spore suspension of Phytophthora infestans.

The plants are placed in an incubation cabin at approximately 20° C. and 100% relative atmospheric humidity.

Evaluation is carried out 3 days after the inoculation. An efficacy of 0% means that the disease level on the treated plants corresponds to that of the untreated control, while an efficacy of 100% means that no disease is observed on the treated plants.

In this test, for example the compounds (IV-2) and (IV-3) of the Preparation Examples exhibit, at an exemplary active compound application rate of 50 g/ha, an efficacy of 96% compared to the untreated control.

Example IV-B

Plasmopara-Test (Grapevines)/protective
Solvent: 47 parts by weight of acetone
Emulsifier: 3 parts by weight of alkylaryl polyglycol ether To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of the active compound until dew-moist. After the spray coating has dried on, the plants are inoculated with an aqueous spore suspension of Plasmopara vilicola and then remain in an incubation cabin at approximately 20° C. and 100% relative atmospheric humidity for 1 day. The plants are subsequently placed in a greenhouse at approximately 21° C. and approximately 90% atmospheric humidity for 5 days. The plants are then moistened and placed in an incubation cabin for 1 day.

Evaluation is carried out 6 days after the inoculation. An efficacy of 0% means that the disease level on the treated plants corresponds to that of the untreated control, while an efficacy of 100% means that no disease is observed on the treated plants.

In this test, for example the compounds of Preparation Examples (IV-2) and (IV-3) exhibit, at an exemplary active compound application rate of 50 g/ha, an efficacy of 96 to 100% compared to the untreated control.

What is claimed is:

1. Compounds of the formula (I-I):

(I-I)

in which
A represents alkylene having 1 to 6 carbon atoms which is optionally mono- or polysubstituted by identical or different substituents, the substituents being selected from the list below:
halogen, cyano, nitro, amino, hydroxyl, formyl, carboxyl, carbamoyl, thiocarbamoyl;
alkoxy, alkylthio, alkylsulphinyl or alkylsulphonyl having in each case 1 to 6 carbon atoms and being in each case straight-chain or branched;
alkenyl or alkenyloxy having in each case 2 to 6 carbon atoms and being in each case straight-chain or branched;
halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
cycloalkyl having 3 to 6 carbon atoms;
and also aryl or heterocyclyl, each of which is optionally mono- or polysubstituted by identical or different substituents selected from the group consisting of halogen, cyano and straight-chain or branched alkyl having 1 to 4 carbon atoms;
straight-chain or branched halogenoalkyl having 1 to 4 carbon atoms and 1 to 9 identical or different halogen atoms;
straight-chain or branched alkoxy or alkylthio having 1 to 4 carbon atoms;
straight-chain or branched halogenoalkoxy or halogenoalkylthio having 1 to 4 carbon atoms and 1 to 9 identical or different halogen atoms;
and allylene or dioxyalkylene having in each case 1 to 6 carbon atoms and being in each case doubly attached and optionally mono- or polysubstituted by identical or different substituents selected from the group consisting of halogen and straight-chain or branched allyl having 1 to 4 carbon atoms;
and straight-chain or branched halogenoalkyl having 1 to 4 carbon atoms and 1 to 9 identical or different halogen atoms,
Q represents oxygen or sulphur,
$R^1$ represents 1,2,3,4-tetrahydronaphthalenyl or 2,3-dihydro-1H-indenyl, each of which is optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
$R^2$ represents one of the groupings below:

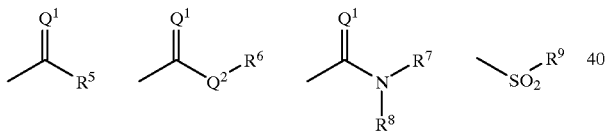

in which
$Q^1$ and $Q^2$ independently of one another each represent oxygen or sulphur,
$R^5$ represents hydrogen or alkyl having 1 to 6 carbon atoms or represents aryl which is optionally substituted by halogen, cyano, nitro, alkyl or alkoxy having in each case 1 to 4 carbon atoms,
$R^6$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
$R^7$ represents hydrogen, alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
$R^8$ represents alkyl having 1 to 6 carbon atoms or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms, or
$R^7$ and $R^8$ together with the linking nitrogen atom represent an optionally methyl-substituted heterocyclic ring,
$R^9$ represents alkyl having 1 to 6 carbon atoms, dialkylamino having in each case 1 to 4 carbon atoms in the individual alkyl moieties, heterocyclyl having 3 to 7 ring members which is attached via nitrogen or represents aryl or arylalkyl having 1 to 4 carbon atoms in the alkyl moiety, each of which is optionally substituted in the aryl moiety by halogen, cyano, nitro, alkyl or alkoxy having in each case 1 to 4 carbon atoms,
$R^3$ represents hydrogen or alkyl having 1 to 4 carbon atoms,
$R^4$ represents aryl, cycloalkyl or cycloalkenyl having 3 to 8 carbon atoms, or heterocyclyl having 3 to 12 ring members, each of which is optionally mono- or polysubstituted by identical or different substituents, the substituents being selected from the list below:
halogen, cyano, nitro, amino, hydroxyl, formyl, carboxyl, carbamoyl, thiocarbamoyl;
alkyl, alkoxy, alkylthio, alkylsulphinyl or alkylsulphonyl having in each case 1 to 6 carbon atoms and being in each case straight-chain or branched;
alkenyl or alkenyloxy having in each case 2 to 6 carbon atoms and being in each case straight-chain or branched;
halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
alkylene or dioxyalkylene having in each case 1 to 6 carbon atoms and being in each case doubly attached and being in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
cycloalkyl having 3 to 6 carbon atoms;
and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of
halogen, cyano and straight-chain or branched alkyl having 1 to 4 carbon atoms;
straight-chain or branched halogenoalkyl having 1 to 4 carbon atoms and 1 to 9 identical or different halogen atoms;
straight-chain or branched alkoxy or alkylthio having 1 to 4 carbon atoms;

straight-chain or branched halogenoalkoxy or halogenoalkylthio having 1 to 4 carbon atoms and 1 to 9 identical or different halogen atoms;

and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

2. Compounds of the formula (I-I) according to claim 1, in which

A represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), each of which is optionally mono- or polysubstituted by identical or different substituents selected from the group consisting of fluorine, chlorine, cyano and methoxy, Q represents oxygen or sulphur, $R^1$ represents 1,2,3,4-tetrahydronaphthalenyl or 2,3-dihydro-1H-indenyl, each of which is optionally mono- or polysubstituted by identical or different substituents selected from the group consisting of fluorine, chlorine, methyl, trifluoromethyl, ethyl, n- and i-propyl;

$R^2$ represents one of the groupings below:

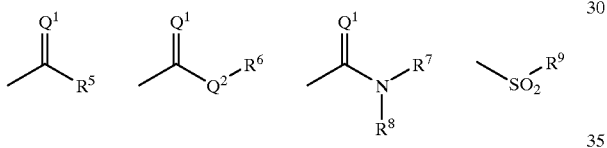

in which $Q^1$ and $Q^2$ independently of one another each represent oxygen or sulphur, $R^5$ represents hydrogen, methyl, ethyl, n- or i-propyl, n-, i-, s- or t-butyl or represents phenyl, which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoro- methoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl.

3. Compounds of the formula (I-I) according to claim 1, in which

A represents methylene, 1-1-ethylene, 1,2-ethylene 1,1-, 1,2-, 1,3- or 2,2-propylene, 1,1-, 1,2-, 1,3-, 1,4,2,2-, 2,3-butylene or 1,1-, 1,2- or 1,3-2-methyl-propylene), each of which is optionally mono- or polysubstituted by identical or different substituents selected from the group consisting of fluorine, chlorine, cyano, methoxy, Q represents 1,2,3,4-tetrahydronaphthalenyl or 2,3-dihydro-1H-indenyl, $R^1$ those mentioned below; each of which is optionally mono- or polysubstituted by identical or different substituents selected from the group consisting of fluorine, chlorine, methyl, trifluoromethyl, ethyl, n- and i-propyl;

$R^2$ represents one of the groupings below:

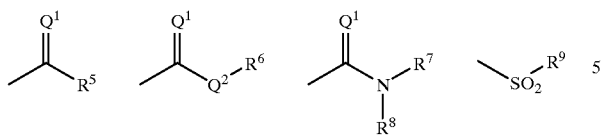

in which
$Q^1$ and $Q^2$ independently of one another each represent oxygen or sulphur, $R^5$ represents hydrogen, methyl, ethyl, n- or i-propyl, n-, i-, s- or t-butyl or represents phenyl, which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^3$ represents hydrogen or represents methyl, $R^4$ represents cyclopropyl, cyclobutyl, cyclopentyl or cyclohexyl, each of which is optionally mono- to hexasubstituted, the substituents being those mentioned below;

represents phenyl, naphthyl, furyl, benzofuranyl, pyrrolyl, indolyl, thienyl, benzothienyl, oxazolyl isoxazolyl, thiazolyl, isothiazolyl, oxadiazolyl, thiadiazolyl, pyridyl quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the substituents being selected from the list below, fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, represents trimethylene (propane-1,3diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl.

4. Compounds of the formula (I-I) according to claim 1, in which

A represents methylene, 1,1-ethylene, 1,2-ethylene, 1,1-propylene, 1,2-propylene, 1,3-propylene or 2,2-propylene, Q represents oxygen, $R^1$ represents 1,2,3,4-tetrahydronaphthalenyl or 2,3-dihydro-1H-indenyl, each of which is optionally substituted by fluorine, $R^2$ represents one of the groupings below:

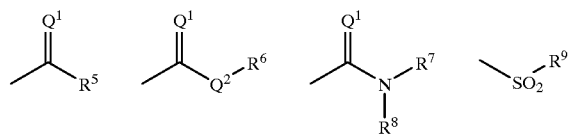

in which
$Q^1$ and $Q^2$ each represent oxygen, $R^5$ represents hydrogen, methyl, ethyl, n- or i-propyl, n-, i-, s- or t-butyl or represents phenyl, which is optionally substituted in the phenyl moiety by fluorine, chlorine, bromine, cyano, nitro, methyl, ethyl, n- or i-propyl, n-, i-, s- or t-butyl, methoxy or ethoxy, $R^6$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, so or t-butyl, methoxy or ethoxy, $R^7$ represents hydrogen, methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, $R^8$ represents methyl, ethyl, n- or i-propyl, n-, i-, s- or t-butyl or represents phenyl, benzyl, 1-phenylethyl or 2-phenylethyl, each of which is optionally substituted in the phenyl moiety by fluorine, chlorine, bromine, cyano, nitro, methyl, ethyl, n- or i-propyl, n-, i-, s- or t-butyl, methoxy or ethoxy, or $R^7$ and $R^8$ together with the linking nitrogen atom represent an optionally methyl-substituted heterocyclic ring, $R^9$ represents methyl, ethyl, n- or i-propyl, n-, i-, s- or t-butyl, dimethylamino, diethylamino, pyrrolidin-1-yl, morpholin-N-yl, piperidin-1-yl, or represents phenyl, benzyl, 1-phenylethyl or 2-phenylethyl, each of which is optionally n-substituted in the phenyl moiety by fluorine, chlorine, bromine, cyano, nitro, methyl, ethyl, n- or i-propyl, n-, i-, s- or t-butyl, methoxy or ethoxy, $R^3$ rep resents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the substituents being selected from the list below:
fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, and
trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

5. Compounds of the formula (II-I);

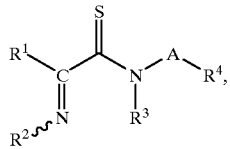

(II-I)

in which
A represents optionally substituted alkylene,
$R^1$ represents 1,2,3,4-tetrahydronaphthalenyl or 2,3-dihydro-1H-indenyl, each of which is optionally substituted,
$R^2$ represents hydroxyl, amino, or represents alkyl, alkenyl, alkinyl, alkoxy, alkenyloxy, alkinyloxy, alkylamino, dialkylamino, arylamino, cycloalkyl, cycloalkenyl, cycloalkoxy, cycloalkenyloxy, cycloalkylamino, aryl, arylalkyl, arylalkoxy or heterocyclyl, each of which is optionally substituted,
$R^3$ represents hydrogen or represents alkyl, alkenyl, alkinyl or cycloalkyl, each of which is optionally substituted,
$R^4$ represents cycloalkyl, cycloalkenyl, aryl or heterocyclyl, each of which is optionally substituted.

6. Compounds of the formula (II-I) according to claim 5, in which
A represents alkylene having 1 to 6 carbon atoms which is optionally mono- or polysubstituted by identical or different substituents, the substituents being selected from the list below:
halogen, cyano, nitro, amino, hydroxyl, formyl, carboxyl, carbamoyl, thiocarbamoyl;
alkoxy, alkylthio, alkylsulphinyl or alkylsulphonyl having in each case 1 to 6 carbon atoms and being in each case straight-chain or branched;
alkenyl or alkenyloxy having in each case 2 to 6 carbon atoms and being in each case straight-chain or branched;
halogenoalkoxy, halogenoalkylthio, halogenolalkylsulphinyl or halogenoalkylsulphonyl having in each case 1 to 6 carbon atoms and 1 to 13 identical or different halogen atoms and being in each case straight-chain or branched;
halogenoalkenyl or halogenoalkenyloxy having in each case 2 to 6 carbon atoms and 1 to 13 identical or different halogen atoms and being in each case straight-chain or branched;
alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;
cycloalkyl having 3 to 6 carbon atoms;
and also aryl or heterocyclyl, each of which is optionally mono- or polysubstituted by identical or different substituents selected from the group consisting of
halogen, cyano and straight-chain or branched alkyl having 1 to 4 carbon atoms:
straight-chain or branched halogenoalkyl having 1 to 4 carbon atoms and 1 to 9 identical or different halogen atoms;
straight-chain or branched alkoxy or alkylthio having 1 to 4 carbon atoms:
straight-chain or branched halogenoalkoxy or halogenoalkylthio having 1 to 4 carbon atoms and 1 to 9 identical or different halogen atoms:
alkylene or dioxyalkylene having in each case 1 to 6 carbon atoms: being in each case doubly attached and optionally mono- or polysubstituted by identical or different substituents selected from the group consisting of halogen and straight-chain or branched alkyl having 1 to 4 carbon atoms:
and straight-chain or branched halogenoalkyl having 1 to 4 carbon atoms and 1 to 9 identical or different halogen atoms,
$R^1$ represents 1,2,3,4-tetrahydronaphthalenyl or 2,3-dihydro-1H-Indenyl each of which is optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;
$R^2$ represents hydroxyl, amino or represents alkyl, alkenyl, alkinyl, alkoxy, alkenyloxy, alkinyloxy, alkylamino, dialkylamino having in each case 1 to 4 carbon atoms in the respective alkyl moieties and being in each case optionally substituted by halogen, cyano or $C_1$–$C_4$-alkoxy, represents cycloalkyl, cycloalkenyl, cycloalkoxy, cycloalkenyloxy, cycloalkylamino, having 3 to 8 carbon atoms in the respective rings and being in each case optionally substituted by halogen, cyano or $C_1$–$C_4$-alkoxy, or represents in each case optionally substituted phenyl, benzyl, benzyloxy, naphthyl, phenylamino or heterocyclyl having 3 to 8 ring members, the substituents being selected from the list below:

halogen, cyano, nitro, amino, hydroxyl, formyl, carboxyl, carbamoyl, thiocarbamoyl;

alkyl, alkoxy, alkylthio, alkylsulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

or cycloalkyl having 3 to 6 carbon atoms, $R^3$ represents hydrogen or alkyl having 1 to 4 carbon atoms, $R^4$ represents aryl, cycloalkyl or cycloalkenyl having 3 to 8 carbon atoms, or heterocyclyl having 3 to 12 ring members, each of which is optionally mono- or polysubstituted by identical or different substituents, the substituents being selected from the list below:

halogen, cyano, nitro, amino, hydroxyl, formyl, carboxyl, carbamoyl thiocarbamoyl;

alkyl alkoxy, alkylthio, a alksulphinyl or alkylsulphonyl having in each case 1 to 6 carbon atoms and being in each case straight-chain or branched;

alkenyl or alkenyloxy having in each case 2 to 6 carbon atoms and being in each case straight-chain or branched;

halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms and being in each case straight-chain or branched;

halogenoalkenyl or halogenoalkenyloxy having in each case 2 to 6 carbon atoms and 1 to 13 identical or different halogen atoms and being in each case straight-chain or branched;

alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties and being in each case straight-chain or branched;

alkylene or dioxyalkylene having in each case 1 to 6 carbon atoms and being in each case doubly attached-and in each case optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms;

cycloalkyl having 3 to 6 carbon atoms;

and also aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, each of which is optionally mono- or polysubstituted by identical or different substituents selected from the group consisting of halogen, cyano and straight-chain or branched alkyl having 1 to 4 carbon atoms;

straight-chain or branched halogenoalkyl having 1 to 4 carbon atoms and 1 to 9 identical or different halogen atoms;

straight-chain or branched alkoxy or alkylthio having 1 to 4 carbon atoms;

straight-chain or branched ,halogenoalkoxy or halogenoalkylthio having 1 to 4 carbon atoms and 1 to 9 identical or different halogen atoms;

and alkylene or dioxyalkylene having in each case 1 to 6 carbon atoms and being in each case doubly attached and optionally mono- or polysubstituted by identical or different substituents selected from the group consisting of halogen and straight-chain or branched alkyl having 1 to 4 carbon atoms and straight-chain or branched halogenoalkyl having 1 to 4 carbon atoms and 1 to 9 identical or different halogen atoms.

7. Compounds of the formula (II-I) according to claim 5, in which

A represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-(2-methyl-propylene), optionally mono- or polysubstituted by identical or different substituents selected from the group consisting of fluorine, chlorine, cyano, methoxy, $R^1$ represents 1,2,3,4-tetrahydronaphthalenyl or 2,3-dihydro-1H-indenyl each of which is optionally mono- or polysubstituted by identical or different substituents selected from the group consisting of fluorine, chlorine, methyl, trifluoromethyl, ethyl, n- and i-propyl;

$R^2$ represents hydroxyl, amino or represents methyl, ethyl, n- or i-propyl, n-, i-, s- or t-butyl, vinyl, allyl, propargyl, methoxy, ethoxy, allyloxy, propargyloxy, methylamino, ethylamino, dimethylamino, each of which is optionally substituted by halogen, cyano, methoxy or ethoxy, represents cyclopropyl, cyclobutyl, cyclopentyl, cyclohexyl, cyclopentyloxy, cyclohexyloxy, cyclopentylamino, cyclohexylamino, each of which is optionally substituted by halogen, cyano, methoxy or ethoxy, or represents phenyl, benzyl, benzyloxy, naphthyl, phenylamino or heterocyclyl having 3 to 8 ring members and being in each case optionally substituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, m- or t-butyl, methoxy, ethoxy, n- or i-propoxy, methylthio, ethylthio, n- or i-propylthio, methylsulphinyl, ethylsulphinyl, methylsulphonyl or ethylsulphonyl, se fluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl, $R^3$ represents hydrogen or represents methyl or ethyl, $R^4$ represents cyclopropyl, cyclobutyl, cyclopentyl or cyclohexyl, phenyl, naphthyl, furyl, benzofuranyl, pyrrolyl, indolyl, thienyl, benzothienyl, oxazolyl, isoxazolyl, thiazolyl, isothiazolyl oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl.

8. Compounds of the formula (II-I) according to claim 5, in which

A represents methylene, 1,1-ethylene, 1,2-ethylene 1,1-, 1,2-, 1,3- or 2,2-propylene, 1,1-, 1,2-, 1,3-, 1,4-, 2,2-, 2,3-butylene or 1,1-, 1,2- or 1,3-2-methyl-propylene), optionally mono- or polysubstituted by identical or different substituents selected from the group consisting of fluorine, chlorine, cyano, methoxy, $R^1$ represents 1,2,3,4-tetrahydronaphthalenyl or 2,3-dihydro-1H-indenyl each of which is optionally mono- or polysubstituted by identical or different substituents selected from the group consisting of fluorine, chlorine, methyl, trifluoromethyl, ethyl, n- and i-propyl;

$R^2$ represents hydroxyl, amino, methyl, fluoromethyl, difluoromethyl, trifluoromethyl, cyanophenyl, ethyl, n- or i-propyl,. n-, i-, s- or t-butyl, vinyl, allyl, methoxy, fluoromethoxy, difluoromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl, $R^3$ represents hydrogen or represents methyl, $R^4$ represents cyclopropyl, cyclobutyl, cyclopentyl or cyclohexyl, each of which is optionally mono to hexasubstituted, the substituents being those mentioned below;

represents phenyl, naphthyl, furyl, benzofuranyl, pyrrolyl, indolyl, thienyl, benzothienyl, oxazolyl, isoxazolyl, thiazolyl, isothiazolyl, oxadiazolyl, thiadiazolyl, pyridyl, quinolyl, pyrimidyl, pyridazinyl, pyrazinyl, oxiranyl, oxetanyl, tetrahydrofuryl, perhydropyranyl, pyrrolidinyl, piperidinyl or morpholinyl, each of which is optionally mono- to trisubstituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, trimethylene (propane-1,3 diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, and cyclopropyl, cyclobutyl, cyclopentyl or cyclohexyl.

9. Compounds of the formula (II-I) according to claim 5, in which

A represents methylene, 1,1-ethylene, 1,2-ethylene, 1,1-propylene, 1,2-propylene, 1,3-propylene, or 2,2-propylene, $R^1$ represents 1,2,3,4-tetrahydronaphthalenyl or 2,3-dihydro-1H-indenyl each of which is optionally substituted by fluorine;

$R^2$ represents hydroxyl, amino, methyl, fluoromethyl, difluoromethyl, trifluoromethyl, cyanophenyl, ethyl, n- or i-propyl, n-, i-, s- or t-butyl, vinyl, allyl, methoxy, fluoromethoxy, difluoromethoxy, trifluoromethoxy, cyanomethoxy, ethoxy, allyloxy, methylamino, ethylamino, dimethylamino, cyclopropyl, cyclobutyl, cyclopentyl, cyclohexyl, cyclopentyloxy, cyclohexyloxy, cyclopentylamino, cyclohexylamino or represents phenyl, benzyl, benzyloxy, naphthyl, phenylamino, pyrrolidin-1-yl, morpholin-N-yl, piperidin-1-yl, benzofuranyl, thienyl, benzothienyl, pyridyl, quinolyl, tetrahydrofuryl or perhydropyranyl, each of which is optionally substituted, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, and trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl, $R^3$ represents hydrogen or methyl, $R^4$ represents cyclohexyl or optionally mono- to trisubstituted phenyl, thienyl, furyl, benzofuryl, benzothienyl, pyridyl, pyrimidinyl, naphthyl, quinolyl, the substituents being selected from the list below:

fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl, methylamino, ethylamino, n- or i-propylamino, dimethylamino, diethylamino, acetyl, propionyl, acetyloxy, methoxycarbonyl, ethoxycarbonyl, methylsulphonyloxy, ethylsulphonyloxy, hydroximinomethyl, hydroximinoethyl, methoximinomethyl, ethoximinomethyl, methoximinoethyl or ethoximinoethyl, and trimethylene (propane-1,3-diyl), tetramethylene (butane-1,4-diyl), methylenedioxy or ethylenedioxy, each of which is doubly attached and each of which is optionally mono- or polysubstituted by identical or different substituents selected from the group consisting of fluorine, chlorine, methyl, trifluoromethyl, ethyl, n- and i-propyl.

10. A pesticidal composition comprising a pesticidally effective amount of at least one compound of the formula (I) according to claim 1 and an extender.

11. A process for preparing a pesticidal composition, said process comprising mixing at least one compound of the formula (I) according to claim 1 with an extender and/or surfactant.

12. A method for controlling pests, said method comprising applying to pests and/or their habitat a pesticidally effective amount of at least one compound of the formula (1) according to claim 1.

13. A pesticidal composition comprising a pesticidally effective amount of at least one compound of the formula (I) according to claim 5 and an extender.

14. A process for preparing a pesticidal composition, said process comprising mixing at least one compound of the formula (I) according to claim 5 with an extender and/or surfactant.

15. A method for controlling pests, said method comprising applying to pests and/or their habitat a pesticidally effective amount of at least one compound of the formula (I) according to claim 5.

\* \* \* \* \*

UNITED STATES PATENT AND TRADEMARK OFFICE
CERTIFICATE OF CORRECTION

PATENT NO. : 6,225,334 B1  
DATED : May 1, 2001  
INVENTOR(S) : Thomas Seitz et al.

It is certified that error appears in the above-identified patent and that said Letters Patent is hereby corrected as shown below:

<u>Column 101,</u>
Line 29, delete "each of which is"

<u>Column 104,</u>
Line 56, "or 1,3-2-methyl…" to -- or 1,3-(2-methyl… --

Signed and Sealed this

Ninth Day of September, 2003

JAMES E. ROGAN
*Director of the United States Patent and Trademark Office*